United States Patent [19]
Ando et al.

[11] Patent Number: 5,424,325
[45] Date of Patent: Jun. 13, 1995

[54] AMINOKETONE DERIVATIVES

[75] Inventors: Ryoichi Ando; Naoko Ando; Hirokazu Masuda, all of Kanagawa; Toshiro Sasaki, Tokyo; Yasuhiro Morinaka, Ibaraki; Chizuko Takahashi, Kanagawa; Yoshikuni Tamao, Tokyo; Akihiro Tobe, Kanagawa, all of Japan

[73] Assignee: Mitsubishi Kasei Corporation, Tokyo, Japan

[21] Appl. No.: 171,695

[22] Filed: Dec. 22, 1993

[30] Foreign Application Priority Data

Dec. 25, 1992 [JP] Japan .................. 4-346928

[51] Int. Cl.$^6$ .............. A61K 31/34; A61K 31/425; C07D 213/30; C07D 213/32
[52] U.S. Cl. .............. 514/357; 514/365; 514/376; 514/438; 514/471; 546/336; 546/337; 548/204; 548/232; 549/77; 564/192
[58] Field of Search .............. 549/77; 514/438, 357, 514/365, 376, 471; 548/204, 232; 546/336, 337; 564/192

[56] References Cited

FOREIGN PATENT DOCUMENTS

| 0214823 | 3/1987 | European Pat. Off. . |
| 0272671 | 6/1988 | European Pat. Off. . |
| 0525420 | 2/1993 | European Pat. Off. . |

*Primary Examiner*—Richard L. Raymond
*Assistant Examiner*—Mary C. Cebulak
*Attorney, Agent, or Firm*—Wenderoth, Lind & Ponack

[57] ABSTRACT

Aminoketone derivatives according to the present invention strongly inhibit thiol protease such as calpain, papain, cathepsin B, cathepsin H, cathepsin L or the like and have excellent properties concerning absorbance on oral administration, tissue distribution and cell membrane permeability. The aminoketone derivatives cart thus be used as therapeutic agents for treating muscular dystrophy, cataract, cardiac infarction, stroke, Alzheimer's disease, amyotrophy, osteoporosis and hypercalcemia and so on. It may also be used as therapeutic agents for preventing metastasis of cancer. In addition, the present derivatives are also applicable as intermediates for the preparation of ketone derivatives, which have inhibitory activity against thiol protease.

5 Claims, No Drawings

AMINOKETONE DERIVATIVES

FIELD OF THE INVENTION

This invention relates to novel aminoketone derivatives and, in particular, to novel aminoketone derivatives and their pharmaceutically acceptable salts which strongly inhibit thiol protease such as papain, cathepsin B, cathepsin H, cathepsin L and calpain or the like.

BACKGROUND OF THE INVENTION

In accordance with the elucidation of the in vivo activity of thiol protease such as papain, cathepsin B, cathepsin H, cathepsin L, calpain or the like, it has been found that their extraordinary hypersthenia causes various diseases. Further, there are increasing reports which show thiol protease inhibitors are effective on such disease in animal models.

It is considered that thiol protease such as calpain, cathepsin B or the like takes part in the initial process such as disappearance of Z line through the decomposition of muscular fiber protein in the collapse of skeletal muscle as seen in muscular diseases such as muscular Dystrophy, amyotrophy or the like [Taisha (Metabolism), 25, extra-edition "Taisha-byo Highlight (Metabolic Diseases Highlight)", 183(1988)]. Furthermore, E-64-d, namely a thiol protease inhibitor, has been reported as having life-prolonging effect in experimental muscular dystrophy hamster [Journal of Pharmacobio dynamics, 10, 678(1987)]. Accordingly, such thiol protease inhibitors are expected to be useful as therapeutic agents for the treatment of muscular dystrophy, amyotrophy or the like.

The main cause of the post-ischemic cellular disorder which occurs during ischemic diseases such as cardiac infarction, stroke and the like is active oxygen produced by xanthine oxidase. It has been reported that, during the ischemia, the increase in $Ca^{2+}$ concentration results in the activation of calpain which restrictively degrade xanthine dehydrogenase, a precursor of xanthine oxidase, to give xanthine oxidase [New England Journal of Medicine, 312, p.159, (1985)]. It has also been reported that the activation of calpain may directly cause the necrosis of myocardial cells or neurocytes [Saishin Igaku, 43, p.783, (1988)]. There have been reports that NCO-700, a calpain inhibitor, is effective on cardiac infarction when tested on animal models [Arzneimittel Forschung/Drug Research, 36, p.190, p.671, (1986)], and that E-64-C inhibits the degradation of microtubule-associated protein after the brain ischemia [Brain Research, 526, p.177, (1990)]. These reports indicate that a calpain inhibitor can be useful for the treatment of ischemic diseases such as cardiac infarction, stroke and the like.

The cause of senile plaque which is found specifically in the brain of patients suffering from Alzheimer's disease is known to be the precipitated amyloid, a protein produced by the decomposition of an amyloid precursor protein (APP). Although APP does not give amyloid as a normal metabolite, it may be converted into amyloid under an abnormal metabolism where protease is extremely activated, and precipitated as senile plaque [Scientific American, (11), p.40, (1991)]. Therefore, protease inhibitor is expected to be useful for the treatment of Alzheimer's disease.

The activation of calpain has been observed in a brain trauma model of rabbit [Neurochemical Research, 16, p.483, (1991)]. It has also been observed that the administration of leupeptin, a calpain inhibitor, can protect axon in brain trauma models of rat [Journal of Neurosurgery, 65, p.92, (1986)]. Thus, calpain inhibitors are considered to be useful for improving the consciousness disturbance or motor disturbance caused by brain trauma.

It has also been reported that myelin-associated protein which exists in dendrite of neurocytes is decomposed by calpain [Journal of Neurochemistry, 47, p.1007, (1986)], indicating that calpain inhibitors may be effective on diseases caused by the demyelination of neurocytes such as multiple sclerosis, peripheral nervous neuropathy and the like.

The main cause of the turbidity during cataract is hydrolytic products of a water-soluble protein crystalline by protease in the lens. It has been observed an increase in calcium concentration in lens of cataractous animal models and some of human cataract [Investigative Ophthalmology & Visual Science, 28, p.1702, (1987); Experimental Eye Research, 34, p.413, (1982)]. The dominant protease contained in lens is calpain [Lens and Eye Toxicity Research, 6, p.725, (1989)]. These facts indicate that the abnormal sthenia of calpain can be one of the causes of cataract. There is a report that E-64, an inhibitor of calpain, is effective on cataract in animal models [Investigative Ophthalmology & Visual Science, 32, p.533, (1991)], indicating that calpain inhibitors can be useful in the treatment of cataract.

Neutrophils, which are deeply associated with inflammation, show the degranulation or production of superoxides in response to the stimulations by a chemotactic factor or phorbol ester through a mechanism which appears to be mediated by protein kinase C (PKC). Calpain participates in the activation of PKC in the manner where it promotes the degranulation and inhibits the production of superoxides [Journal of Biological Chemistry, 263, p.1915, (1988)]. In another report, the concentration of cathepsin B in macrophage in rat is 30 to 40 times that of leukocytes and neutrophils, and the concentration of enzyme in inflammatory macrophage is 6 times that of normal macrophage [Journal of Biochemistry, 98, p.87, (1985)]. These facts indicate that thiol protease inhibitors are useful as anti-inflammatory drugs.

The type I allergy reaction is mediated by immunoglobulin E (IgE) produced in a subject immunized with an antigen. Estatin A, a thiol protease inhibitor, has been reported to specifically inhibit the production of IgE without affecting on the production of IgG [The Journal of Antibiotics, 42, p.1362, (1989)]. Accordingly, thiol protease inhibitors are considered to be useful as antiallergic drugs.

In case of necrosis of hepatic cells, it is believed that impairment of the cell membrane leads to an increase in the permeability of $Ca^{2+}$, an increase in intracellular $Ca^{2+}$ concentration, an activation of calpain, and, as the result, the decomposition of its substrate such as skeletal protein takes place, which results in the death of cells. Accordingly, a calpain inhibitor can be used as a therapeutic agent for fulminant hepatitis.

Cathepsins such as cathepsin B and cathepsin L are involved in decomposition of bone collagen in osteoclast. It has been reported that administration of an inhibitor of cathepsins, E-64 or estatin A, to a rat which has an enhanced bone destruction by administration of parathyroid hormone leads to a decrease of calcium concentration and hydroxyproline concentration in blood [Biochemical and Biophysical Research Communication, 125, p.441, (1984): Japanese Patent Publication (kokai) No. 218610/1990]. Accordingly, it is believed that an inhibitor of cathepsins can be a therapeutic agent for osteoporosis, hypercalcemia and the like.

There exist, as a substrate for calpain, sex hormone receptors such as estrogen receptor and androgen receptor, and it is known that calpain activates these receptors. Accordingly, it is considered that an abnormal sthenia of calpain causes a disease which is suspected to be caused by an abnormal activation of the sex hormone receptors, for example, breast carcinoma, prostatic carcinoma or prostatomegaly. It is believed that an inhibitor for calpain can be a therapeutic agent for the above disease.

Receptors for epidermal growth factor (EGF) are also considered to be activated in association with the canceration of cells. It is known that calpain activates the EGF receptors as its substrate. Furthermore, it has been reported that calpain is activated in cells which have been infected with adult T cell human leukocyte virus (ATLV/HTLV-1) [Seikagaku, 57, p.1202, (1985)]. On the other hand, it is said that cathepsin B is greatly involved in a process of cancer metastasis because it accelerates decomposition of collagen which is a important step for the cancer metastasis or directly decompose collagen, and because it has a profound correlation with plasma membrane of neoplastic cells [Tumor Progression and Markers, p.47, (1982); Journal of Biological Chemistry, 256, p.8536, (1981)]. These facts suggest that a thiol protease inhibitor has an ability to suppress the growth of cancer cells and prevent the metastasis of cancer.

Activation of platelet causes the aggregation thereof which is a cause of thrombus. It has been reported that an inhibitor of calpain, E-64-d, suppressed aggregation of platelet caused by thrombin [Thrombosis Research, 57, p.847, (1990)]. Accordingly, the inhibitor of calpain can be used as an inhibitor against aggregation of platelet.

As described above, an abnormal sthenia of thiol protease causes various diseases and a validity of several thiol protease inhibitors in animal models has been reported. However, most of the known inhibitors, for example, epoxy succinate derivatives such as E-64 [Agricultural and Biological Chemistry, 42, p.529, (1978)], E-64-d [Journal of Biochemistry, 93, p.1305, (1983)], NCO-700 [Japanese Patent Publication (kokai) No. 126879/1983], and estatins A and B [The Journal of Antibiotics, 42, p.1362, (1989)] or α-substituted ketone of a peptide such as chloromethyl ketone [Journal of Biochemistry, 99, p.173, (1986)] and acyloxymethyl ketone [Biochemistry, 30, p.4678, (1991)] are irreversible inhibitors. It is generally said that the irreversible inhibitors are highly toxic because they are liable to react with non-specifically with components constituting the living body, other than target enzymes. Therefore, there have been few compounds applicable to clinical use so far. Although peptidyl aldehydes such as leupeptin [The Journal of Antibiotics, 22, p.283, (1969)] or calpeptin [Journal of Enzyme Inhibition, 3, p.195, (1990)] are known as reversible inhibitors, they also have problems in chemical and in vivo stabilities, cell membrane permeabilities and the like.

SUMMARY OF THE INVENTION

The present inventors investigated into various compounds with the aim of developing reversible inhibitors against thiol protease, which have excellent properties in absorbance on oral administration, tissue distribution and cell membrane permeability, and have found that certain derivatives of ketone have such desired properties.

More particularly, the subject matter of the present invention is directed to an aminoketone derivative having the general formula (I) or a pharmaceutically acceptable salt thereof:

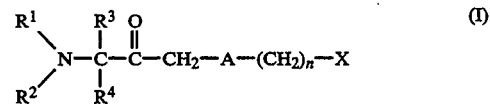

wherein,
R$^1$ is hydrogen,

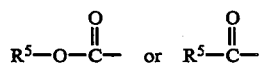

(R$^5$ is selected from the group consisting of C$_1$ to C$_{20}$ alkyl optionally substituted by one or more substituents selected from the group consisting of C$_6$ to C$_{14}$ aryl optionally substituted by one or more substituents, fluorenyl, a heterocyclic residue optionally substituted by one or more substituents, C$_3$ to C$_{15}$ cycloalkyl, C$_3$ to C$_{15}$ cycloalkyloxy, C$_6$ to C$_{14}$ aryloxy optionally substituted by one or more substituents, C$_7$ to C$_{20}$ aralkyloxy optionally substituted by one or more substituents, C$_6$ to C$_{14}$ arylthio optionally substituted by one or more substituents, hydroxyl and C$_2$ to C$_{10}$ acyloxy; C$_2$ to C$_{10}$ alkenyl optionally substituted by C$_6$ to C$_{14}$ aryl optionally substituted by one or more substituents or by a heterocyclic residue optionally substituted by one or more substituents; C$_6$ to C$_{14}$ aryl optionally substituted by one or more substituents; and a heterocyclic residue optionally substituted by one or more substituents), R$^2$ and R$^4$ are independently hydrogen or C$_1$ to C$_5$ alkyl, R$^3$ is hydrogen, C$_1$ to C$_{20}$ alkyl optionally substituted by one or more substituents, or C$_6$ to C$_{14}$ aryl optionally substituted by one or more substituents, or when R$^3$ and R$^4$ are taken together, they are C$_1$ to C$_{10}$ alkylene, —A— is an oxygen atom, a sulfur atom or

(R$^6$ is hydrogen or C$_1$ to C$_5$ alkyl), n is an integer of from 1 to 10, and X is a heterocyclic residue optionally substituted by one or more substituents.

DETAILED DESCRIPTION OF THE INVENTION

The present invention is described in detail below. A compound according to the present invention is an aminoketone derivative having the general formula (I) or a pharmaceutically acceptable salt thereof:

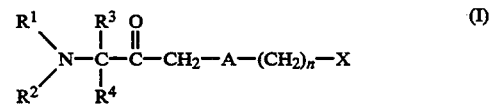

wherein,
R$^z$ is hydrogen,

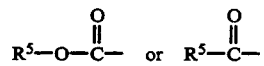

($R^5$ is selected from the group consisting of $C_1$ to $C_{20}$ alkyl (methyl, decyl, icocyl, etc.) optionally substituted by one or more substituents selected from the group consisting of $C_6$ to $C_{14}$ aryl (phenyl, naphthyl, anthryl, etc.) optionally substituted by one or more substituents [one or more substituents selected from the group (hereinafter, referred to as "Group 1") consisting of a halogen atom (a fluorine atom, a chlorine atom, a bromine atom, an iodine atom, etc.), $C_1$ to $C_5$ alkyl (methyl, propyl, pentyl, etc.), trifluoromethyl, $C_1$ to $C_5$ alkoxy (methoxy, propoxy, pentyloxy, etc.), $C_1$ to $C_5$ cyclic acetal residue (methylenedioxy, propylenedioxy, amylenedioxy, etc.), hydroxyl group, $C_2$ to $C_6$ acyloxy (acetoxy, butyryloxy, valeryloxy, etc.), carboxyl, $C_2$ to $C_6$ alkoxycarbonyl (methoxycarbonyl, propoxycarbonyl, pentyloxycarbonyl, etc.), oxo, $C_2$ to $C_6$ acyl (acetyl, butyryl, valeryl, etc.), amino, $C_1$ to $C_5$ monoalkylamino (methylamino, propylamino, pentylamino, etc.), $C_2$ to $C_{10}$ dialkylamino (dimethylamino, methylpropylamino, diisopropylamino, etc.), $C_2$ to $C_6$ acylamino (acetylamino, valerylamino, etc.), carbamoyl, $C_2$ to $C_6$ alkylcarbamoyl (methylcarbamoyl, propylcarbamoyl, pentylcarbamoyl, etc.), $C_6$ to $C_{14}$ aryl (phenyl, naphthyl, anthryl, etc.), $C_6$ to $C_{14}$ aryloxy (phenoxy, naphthyloxy, etc.) and $C_6$ to $C_{14}$ arylamino (phenylamino, naphthylamino, etc.),] fluorenyl, a heterocyclic residue [a heterocyclic residue (hereinafter, referred to as "Group 2") having a ring of 5 to 10 atoms including 1 to 4 hetero atoms selected from the group consisting of oxygen atom, sulfur atom and nitrogen atom, e.g., furan, dihydrofuran, tetrahydrofuran, pyran, dihydropyran, tetrahydropyran, benzofuran, dihydrobenzofuran, isobenzofuran, chromene, chroman, isochroman, thiophene, benzothiophene, pyrrole, pyrroline, pyrrolidine, imidazole, imidazoline, imidazolidine, pyrazole, pyrazoline, pyrazolidine, triazole, tetrazole, pyridine, pyridineoxide, piperidine, pyrazine, piperazine, pyrimidine, pyridazine, indolizine, indole, indoline, isoindole, isoindoline, indazole, benzimidazole, purine, quinolizine, quinoline, phthalazine, naphtyridine, quinoxaline, quinazoline, cinnoline, pteridine, oxazole, oxazolidine, isooxazole, isoxazolidine, thiazole, thiazolidine, isothiazole, isothiazolidine, dioxane, dithian, morpholine, thiomorpholine) optionally substituted by one or more substituents (selected from the Group 1), $C_3$ to $C_{15}$ cycloalkyl (cyclopropyl, cyclononyl, cyclopentadecyl, etc.), $C_3$ to $C_{15}$ cycloalkyloxy (cyclopropyloxy, cyclononyloxy, pentadecyloxy, etc.), $C_6$ to $C_{14}$ aryloxy (phenoxy, naphthyloxy, anthryloxy, etc.) optionally substituted by one or more substituents (selected from the Group 1), $C_7$ to $C_{20}$ aralkyloxy (benzyloxy, phenylpentyloxy, naphthylmethoxy, naphthylethoxy, anthrylmethoxy, etc.) optionally substituted by one or more substituents (selected from the Group 1), $C_6$ to $C_{14}$ arylthio (phenylthio, naphthylthio, anthrylthio, etc.) optionally substituted by one or more substituents (selected from the Group 1), hydroxyl and $C_2$ to $C_{10}$ acyloxy (acetylamino, valeryloxy, benzoyloxy, etc.); $C_2$ to $C_{10}$ alkenyl (vinyl, hexenyl, decenyl, etc.) optionally substituted by $C_6$ to $C_{14}$ aryl (phenyl, naphthyl, anthryl) optionally substituted by one or more substituents (selected from the Group 1) or by a heterocyclic residue (Group 2) optionally substituted by one or more substituents (selected from the Group 1); $C_6$ to $C_{14}$ aryl (phenyl, naphthyl, anthryl, etc.) optionally substituted by one or more substituents (selected from the Group 1); and a heterocyclic residue (Group 2) optionally substituted by one or more substituents (selected from the Group 1)]; $R^2$ and $R^4$ are independently hydrogen or $C_1$ to $C_5$ alkyl (methyl, propyl, pentyl, etc.); $R^3$ is hydrogen, $C_1$ to $C_{20}$ alkyl (methyl, decyl, icocyl, etc.) optionally substituted by one or more substituents [selected from the group consisting of a halogen atom (a fluorine atom, a chlorine atom, a bromine atom, an iodine atom, etc.), $C_3$ to $C_{15}$ cycloalkyl (cyclopropyl, cyclononyl, cyclopentadecyl, etc.), hydroxyl group, $C_1$ to $C_5$ alkoxy (methoxy, propoxy, pentyloxy, etc.) optionally substituted by a heterocyclic residue (Group 2), $C_6$ to $C_{14}$ aryloxy (phenoxy, naphthyloxy, anthryloxy, etc.), $C_7$ to $C_{20}$ aralkyloxy (benzyloxy, phenylpentyloxy, naphthylmethoxy, naphthylethoxy, anthrylmethoxy, etc.), mercapto, $C_1$ to $C_5$ alkylthio (methylthio, propylthio, pentylthio, etc.) optionally substituted by a heterocyclic residue (Group 2), $C_6$ to $C_{14}$ arylthio (phenylthio, naphthylthio, anthrylthio, etc.), $C_7$ to $C_{20}$ aralkylthio (benzylthio, phenylethylthio, naphthylmethylthio, naphthylethylthio, etc.), carboxyl, carbamoyl, $C_2$ to $C_6$ alkoxycarbonyl (methoxycarbonyl, propoxycarbonyl, pentyloxycarbonyl, etc.), a heterocyclic residue (Group 2), amino, $C_1$ to $C_5$ monoalkylamino (methylamino, propylamino, pentylamino, etc.), $C_2$ to $C_{10}$ dialkylamino (dimethylamino, ethylmethylamino, dipentylamino, etc.), $C_2$ to $C_6$ alkoxycarbonylamino (methoxycarbonylamino, propoxycarbonylamino, pentyloxycarbonylamino, etc.), $C_2$ to $C_6$ acylamino (acetylamino, valerylamino, etc.), guanidyl, oxo and $C_6$ to $C_{14}$ aryl (phenyl, naphthyl, anthryl, etc.)] or $C_6$ to $C_{14}$ aryl (phenyl, naphthyl, anthryl, etc.) optionally substituted by one or more substituents (selected from the Group 1), or when $R^3$ and $R^4$ are taken together, they are $C_1$ to $C_{10}$ alkylene (methylene, pentylene, octylene, etc.), —A— is an oxygen atom, a sulfur atom or a group represented by

$R^6$ is hydrogen or $C_1$ to $C_5$ alkyl (methyl, propyl, pentyl, etc.)], n is an integer of from 1 to 10, and X is a heterocyclic residue (Group 2) optionally substituted by one or more substituents (selected from the Group 1).

The aminoketone derivatives having the formula (I) according to the present invention are able to form salts. Specific examples of these salts are, in the presence of an acid group, metal salts such as a lithium salt, a sodium salt, a potassium salt, a magnesium salt and a calcium salt or ammonium salts such as an ammonium salt, a methyl ammonium salt, a dimethyl ammonium salt, a trimethyl ammonium salt and a dicyclohexyl ammonium salt and, in the presence of a base group, mineral acid salts such as hydrochloride, hydrobromide, sulfate, nitrate and phosphate or organic acid salts such as methane sulfonate, benzene sulfonate, paratoluene sulfonate, acetate, propionate, tartarate, fumatate, maleate, malate, oxalate, succinate, citrate, benzoate, mandelate, cinnamate and lactate.

The stereochemistry of the double bond of the aminoketone derivatives having the formula (I) is either one of E, Z and EZ. In addition, the stereochemical configuration of the asymmetric carbon is independently specified by either one of R, S and RS.

Examples of the aminoketone derivatives having the formula (I) are set forth in Table 1 below.

TABLE 1

| Comp. No. | R¹ | R² | R³ | R⁴ | —A—(CH$_2$)$_n$—X |
|---|---|---|---|---|---|
| 1 | (CH$_3$)$_3$COC(O)— | H | H | H | —S—CH$_2$-(2-furyl) |
| 2 | PhCH$_2$OC(O)— | H | H | H | —S—CH$_2$-(2-furyl) |
| 3 | H | H | H | H | —S—CH$_2$-(2-furyl) |
| 4 | (CH$_3$)$_3$COC(O)— | H | H | H | —S—CH$_2$-(3-furyl) |
| 5 | PhCH$_2$OC(O)— | H | H | H | —S—CH$_2$-(3-furyl) |
| 6 | H | H | H | H | —S—CH$_2$-(3-furyl) |
| 7 | (CH$_3$)$_3$COC(O)— | H | H | H | —S—CH$_2$-(2-thienyl) |
| 8 | PhCH$_2$OC(O)— | H | H | H | —S—CH$_2$-(2-thienyl) |
| 9 | H | H | H | H | —S—CH$_2$-(2-thienyl) |
| 10 | (CH$_3$)$_3$COC(O)— | H | H | H | —S—CH$_2$-(3-thienyl) |
| 11 | PhCH$_2$OC(O)— | H | H | H | —S—CH$_2$-(3-thienyl) |
| 12 | H | H | H | H | —S—CH$_2$-(3-thienyl) |
| 13 | (CH$_3$)$_3$COC(O)— | H | H | H | —S—CH$_2$-(2-pyridyl) |

TABLE 1-continued

| # | (col A) | (col B) | (col C) | (col D) | (col E) |
|---|---|---|---|---|---|
| 14 | PhCH₂OC(O)— | H | H | H | —S—CH₂-(2-pyridyl) |
| 15 | H | H | H | H | —S—CH₂-(2-pyridyl) |
| 16 | (CH₃)₃COC(O)— | H | H | H | —S—CH₂-(3-pyridyl) |
| 17 | PhCH₂OC(O)— | H | H | H | —S—CH₂-(3-pyridyl) |
| 18 | H | H | H | H | —S—CH₂-(3-pyridyl) |
| 19 | (CH₃)₃COC(O)— | H | H | H | —S—CH₂-(4-pyridyl) |
| 20 | PhCH₂OC(O)— | H | H | H | —S—CH₂-(4-pyridyl) |
| 21 | H | H | H | H | —S—CH₂-(4-pyridyl) |
| 22 | (CH₃)₃COC(O)— | H | CH₃— | H | —S—CH₂-(2-furyl) |
| 23 | PhCH₂OC(O)— | H | CH₃— | H | —S—CH₂-(2-furyl) |
| 24 | H | H | CH₃— | H | —S—CH₂-(2-furyl) |
| 25 | (CH₃)₃COC(O)— | H | CH₃— | H | —S—CH₂-(2-thienyl) |
| 26 | PhCH₂OC(O)— | H | CH₃— | H | —S—CH₂-(2-thienyl) |
| 27 | H | H | CH₃— | H | —S—CH₂-(2-thienyl) |

TABLE 1-continued

| | | | | | |
|---|---|---|---|---|---|
| 28 | (CH₃)₃COC(O)— | H | CH₃— | CH₃— | —S—CH₂-(2-furyl) |
| 29 | PhCH₂OC(O)— | H | CH₃— | CH₃— | —S—CH₂-(2-furyl) |
| 30 | H | H | CH₃— | CH₃— | —S—CH₂-(2-furyl) |
| 31 | (CH₃)₃COC(O)— | H | CH₃— | CH₃— | —S—CH₂-(2-pyridyl) |
| 32 | PhCH₂OC(O)— | H | CH₃— | CH₃— | —S—CH₂-(2-pyridyl) |
| 33 | H | H | CH₃— | CH₃— | —S—CH₂-(2-pyridyl) |
| 34 | (CH₃)₃COC(O)— | H | CH₃— | CH₃— | —S—CH₂-(3-pyridyl) |
| 35 | PhCH₂OC(O)— | H | CH₃— | CH₃— | —S—CH₂-(3-pyridyl) |
| 36 | H | H | CH₃— | CH₃— | —S—CH₂-(3-pyridyl) |
| 37 | (CH₃)₃COC(O)— | H | CH₃— | CH₃— | —S—CH₂-(4-pyridyl) |
| 38 | PhCH₂OC(O)— | H | CH₃— | CH₃— | —S—CH₂-(4-pyridyl) |
| 39 | H | H | CH₃— | CH₃— | —S—CH₂-(4-pyridyl) |
| 40 | (CH₃)₃COC(O)— | H | (CH₃)₂CH— | H | —S—CH₂-(2-furyl) |
| 41 | PhCH₂OC(O)— | H | (CH₃)₂CH— | H | —S—CH₂-(2-furyl) |

TABLE 1-continued

| 42 | H | H | (CH$_3$)$_2$CH— | H | 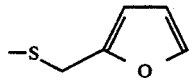 |
| 43 | (CH$_3$)$_3$COC(O)— | H | (CH$_3$)$_2$CH— | H | 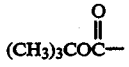 |
| 44 | C$_6$H$_5$CH$_2$OC(O)— | H | (CH$_3$)$_2$CH— | H | 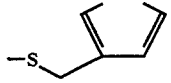 |
| 45 | H | H | (CH$_3$)$_2$CH— | H | 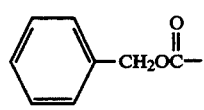 |
| 46 | (CH$_3$)$_3$COC(O)— | H | CH$_3$CH$_2$CH$_2$— | H | 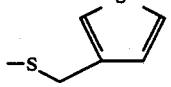 |
| 47 | C$_6$H$_5$CH$_2$OC(O)— | H | CH$_3$CH$_2$CH$_2$— | H | 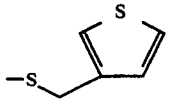 |
| 48 | H | H | CH$_3$CH$_2$CH$_2$— | H |  |
| 49 | (CH$_3$)$_3$COC(O)— | H | CH$_3$CH$_2$CH$_2$— | H | 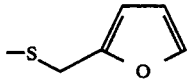 |
| 50 | C$_6$H$_5$CH$_2$OC(O)— | H | CH$_3$CH$_2$CH$_2$— | H | 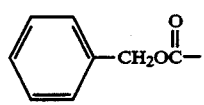 |
| 51 | H | H | CH$_3$CH$_2$CH$_2$— | H | 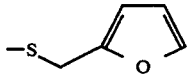 |
| 52 | (CH$_3$)$_3$COC(O)— | H | (CH$_3$)$_2$CHCH$_2$— | H | 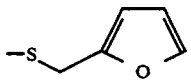 |
| 53 | C$_6$H$_5$CH$_2$OC(O)— | H | (CH$_3$)$_2$CHCH$_2$— | H | 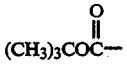 |
| 54 | H | H | (CH$_3$)$_2$CHCH$_2$— | H | 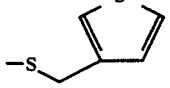 |
| 55 | (CH$_3$)$_3$COC(O)— | H | (CH$_3$)$_2$CHCH$_2$— | H | 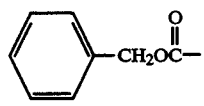 |

TABLE 1-continued

| # | | | | | |
|---|---|---|---|---|---|
| 56 | PhCH₂C(O)O– | H | (CH₃)₂CHCH₂– | H | –S–CH₂-(3-thienyl) |
| 57 | H | H | (CH₃)₂CHCH₂– | H | –S–CH₂-(3-thienyl) |
| 58 | (CH₃)₃CC(O)O– | H | CH₃CH₂CH₂CH₂– | H | –S–CH₂-(2-furyl) |
| 59 | C₆H₁₁CH₂C(O)O– | H | CH₃CH₂CH₂CH₂– | H | –S–CH₂-(2-furyl) |
| 60 | PhCH₂C(O)O– | H | CH₃CH₂CH₂CH₂– | H | –S–CH₂-(2-furyl) |
| 61 | H | H | CH₃CH₂CH₂CH₂– | H | –S–CH₂-(2-furyl) |
| 62 | PhCH₂CH₂C(O)O– | H | CH₃CH₂CH₂CH₂– | H | –S–CH₂-(2-furyl) |
| 63 | PhCH₂CH₂CH₂C(O)O– | H | CH₃CH₂CH₂CH₂– | H | –S–CH₂-(2-furyl) |
| 64 | (1-naphthyl)CH₂C(O)O– | H | CH₃CH₂CH₂CH₂– | H | –S–CH₂-(2-furyl) |
| 65 | (2-naphthyl)CH₂C(O)O– | H | CH₃CH₂CH₂CH₂– | H | –S–CH₂-(2-furyl) |
| 66 | PhOCH₂C(O)O– | H | CH₃CH₂CH₂CH₂– | H | –S–CH₂-(2-furyl) |
| 67 | (3-CH₃O-C₆H₄)OCH₂C(O)O– | H | CH₃CH₂CH₂CH₂– | H | –S–CH₂-(2-furyl) |

TABLE 1-continued

| # | R1 | | R2 | R3 |
|---|---|---|---|---|
| 68 | PhCH=CHC(O)CH3 (4-phenyl-3-buten-2-one) | H | CH3CH2CH2CH2— | H | —S-CH2-furan(2-yl) |
| 69 | 2,4-(CH3O)2-C6H3-CH=CH-C(O)CH3 | H | CH3CH2CH2CH2— | H | —S-CH2-furan(2-yl) |
| 70 | thiazol-4-yl-CH=CH-C(O)CH3 | H | CH3CH2CH2CH2— | H | —S-CH2-furan(2-yl) |
| 71 | 2-(CH3C(O)NH)-thiazol-4-yl-CH=CH-C(O)CH3 | H | CH3CH2CH2CH2— | H | —S-CH2-furan(2-yl) |
| 72 | thiazol-4-yl-CH2-C(O)— | H | CH3CH2CH2CH2— | H | —S-CH2-furan(2-yl) |
| 73 | 2-(H2N)-thiazol-4-yl-CH2-C(O)— | H | CH3CH2CH2CH2— | H | —S-CH2-furan(2-yl) |
| 74 | 2-(CH3C(O)NH)-thiazol-4-yl-CH2-C(O)— | H | CH3CH2CH2CH2— | H | —S-CH2-furan(2-yl) |
| 75 | 2-(PhNH)-thiazol-4-yl-CH2-C(O)— | H | CH3CH2CH2CH2— | H | —S-CH2-furan(2-yl) |
| 76 | (CH3)3C-C(O)— | H | CH3CH2CH2CH2— | H | —S-CH2-furan(3-yl) |
| 77 | PhCH2-C(O)— | H | CH3CH2CH2CH2— | H | —S-CH2-furan(3-yl) |
| 78 | H | H | CH3CH2CH2CH2— | H | —S-CH2-furan(3-yl) |
| 79 | (CH3)3C-C(O)— | H | CH3CH2CH2CH2— | H | —S-CH2-thiophen(2-yl) |

TABLE 1-continued
| | | | | | |
|---|---|---|---|---|---|
| 80 | 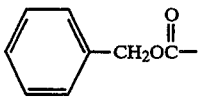 | H | CH₃CH₂CH₂CH₂— | H | 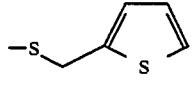 |
| 81 | H | H | CH₃CH₂CH₂CH₂— | H | 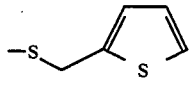 |
| 82 | 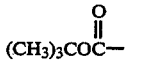 | H | CH₃CH₂CH₂CH₂— | H | 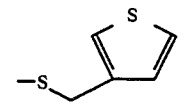 |
| 83 | 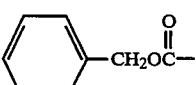 | H | CH₃CH₂CH₂CH₂— | H | 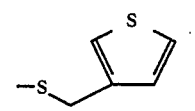 |
| 84 | H | H | CH₃CH₂CH₂CH₂— | H | 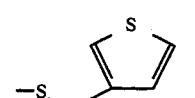 |
| 85 | 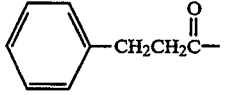 | H | CH₃CH₂CH₂CH₂— | H | 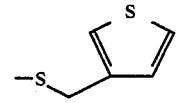 |
| 86 | 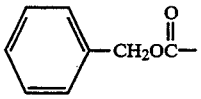 | H | CH₃CH₂CH₂CH₂— | H | 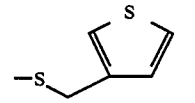 |
| 87 | 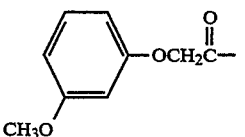 | H | CH₃CH₂CH₂CH₂— | H | 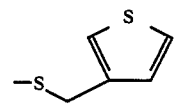 |
| 88 | 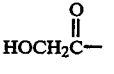 | H | CH₃CH₂CH₂CH₂— | H | 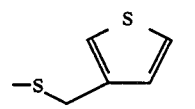 |
| 89 |  | H | CH₃CH₂CH₂CH₂— | H | 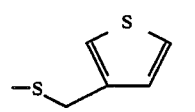 |
| 90 | 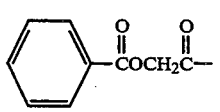 | H | CH₃CH₂CH₂CH₂— | H | 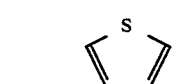 |
| 91 | 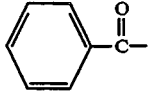 | H | CH₃CH₂CH₂CH₂— | H | 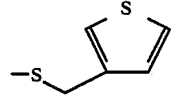 |
| 92 | 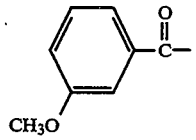 | H | CH₃CH₂CH₂CH₂— | H | 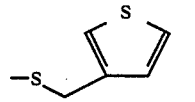 |

TABLE 1-continued

| # | (col A) | (col B) | (col C) | (col D) | (col E) |
|---|---|---|---|---|---|
| 93 | 3-phenoxybenzoyl- (3-PhO-C6H4-C(=O)-) | H | CH3CH2CH2CH2— | H | —S—CH2-(3-thienyl) |
| 94 | (CH3)3COC(=O)— | H | CH3CH2CH2CH2— | H | —S—CH2-(2-pyridyl) |
| 95 | C6H5CH2OC(=O)— | H | CH3CH2CH2CH2— | H | —S—CH2-(2-pyridyl) |
| 96 | H | H | CH3CH2CH2CH2— | H | —S—CH2-(2-pyridyl) |
| 97 | (CH3)3COC(=O)— | H | CH3CH2CH2CH2— | H | —S—CH2-(3-pyridyl) |
| 98 | C6H5CH2OC(=O)— | H | CH3CH2CH2CH2— | H | —S—CH2-(3-pyridyl) |
| 99 | H | H | CH3CH2CH2CH2— | H | —S—CH2-(3-pyridyl) |
| 100 | (CH3)3COC(=O)— | H | CH3CH2CH2CH2— | H | —S—CH2-(4-pyridyl) |
| 101 | C6H5CH2OC(=O)— | H | CH3CH2CH2CH2— | H | —S—CH2-(4-pyridyl) |
| 102 | H | H | CH3CH2CH2CH2— | H | —S—CH2-(4-pyridyl) |
| 103 | (CH3)3COC(=O)— | H | CH3CH2CH2CH2— | H | —S—CH2CH2-(2-furyl) |
| 104 | C6H5CH2OC(=O)— | H | CH3CH2CH2CH2— | H | —S—CH2CH2-(2-furyl) |
| 105 | H | H | CH3CH2CH2CH2— | H | —S—CH2CH2-(2-furyl) |

TABLE 1-continued

| # | R1 | R2 | R3 | R4 | R5 |
|---|----|----|----|----|----|
| 106 | (CH₃)₃COC(O)– | H | CH₃CH₂CH₂CH₂– | H | –S-CH₂CH₂CH₂-(2-furyl) |
| 107 | PhCH₂OC(O)– | H | CH₃CH₂CH₂CH₂– | H | –S-CH₂CH₂CH₂-(2-furyl) |
| 108 | H | H | CH₃CH₂CH₂CH₂– | H | –S-CH₂CH₂CH₂-(2-furyl) |
| 109 | (CH₃)₃COC(O)– | H | cyclohexyl-CH₂– | H | –S-CH₂-(2-furyl) |
| 110 | PhCH₂OC(O)– | H | cyclohexyl-CH₂– | H | –S-CH₂-(2-furyl) |
| 111 | H | H | cyclohexyl-CH₂– | H | –S-CH₂-(2-furyl) |
| 112 | (CH₃)₃COC(O)– | H | cyclohexyl-CH₂– | H | –S-CH₂-(3-thienyl) |
| 113 | PhCH₂OC(O)– | H | cyclohexyl-CH₂– | H | –S-CH₂-(3-thienyl) |
| 114 | H | H | cyclohexyl-CH₂– | H | –S-CH₂-(3-thienyl) |
| 115 | (CH₃)₃COC(O)– | H | (CH₃)₃COC(O)– | H | –S-CH₂-(2-furyl) |
| 116 | PhCH₂OC(O)– | H | CH₃OC(O)CH₂CH₂– | H | –S-CH₂-(2-furyl) |
| 117 | H | H | CH₃OC(O)CH₂CH₂– | H | –S-CH₂-(2-furyl) |
| 118 | (CH₃)₃COC(O)– | H | CH₃OC(O)CH₂CH₂– | H | –S-CH₂-(3-thienyl) |
| 119 | PhCH₂OC(O)– | H | CH₃OC(O)CH₂CH₂– | H | –S-CH₂-(3-thienyl) |

TABLE 1-continued
| | | | | | |
|---|---|---|---|---|---|
| 120 | H | H | CH₃OCCH₂CH₂— (O on C) | H | 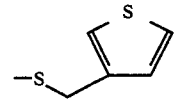 |
| 121 | (CH₃)₃COC(=O)— | H | HOCCH₂CH₂— (O) | H | 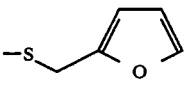 |
| 122 | PhCH₂OC(=O)— | H | HOCCH₂CH₂— (O) | H | 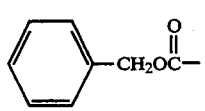 |
| 123 | H | H | HOCCH₂CH₂— (O) | H | 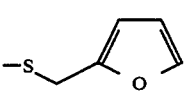 |
| 124 | (CH₃)₃COC(=O)— | H | HOCCH₂CH₂— (O) | H | 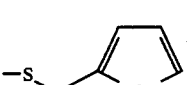 |
| 125 | PhCH₂OC(=O)— | H | HOCCH₂CH₂— (O) | H | 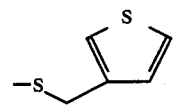 |
| 126 | H | H | HOCCH₂CH₂— (O) | H | 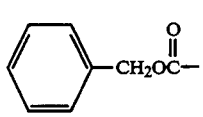 |
| 127 | (CH₃)₃COC(=O)— | H | —CH₃CH₂CH₂CH₂— | | 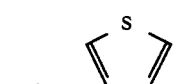 |
| 128 | PhCH₂OC(=O)— | H | —CH₂CH₂CH₂CH₂— | | 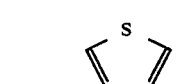 |
| 129 | H | H | —CH₂CH₂CH₂CH₂— | | 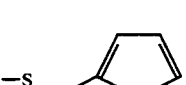 |
| 130 | (CH₃)₃COC(=O)— | H | —CH₂CH₂CH₂CH₂CH₂— | | 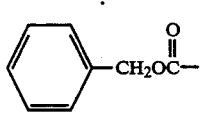 |
| 131 | PhCH₂OC(=O)— | H | —CH₂CH₂CH₂CH₂CH₂— | | 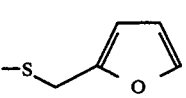 |
| 132 | H | H | —CH₂CH₂CH₂CH₂CH₂— | | 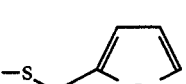 |
| 133 | (CH₃)₃COC(=O)— | H | —CH₂CH₂CH₂CH₂CH₂— | | 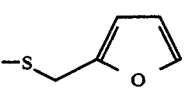 |

| | | | | |
|---|---|---|---|---|
| 134 | PhCH₂OC(O)– | H | –CH₂CH₂CH₂CH₂– | –S–CH₂-(3-thienyl) |
| 135 | H | H | –CH₂CH₂CH₂CH₂– | –S–CH₂-(3-thienyl) |
| 136 | (CH₃)₃COC(O)– | H | –CH₂CH₂CH₂CH₂– | –S–CH₂-(2-pyridyl) |
| 137 | PhCH₂OC(O)– | H | –CH₂CH₂CH₂CH₂– | –S–CH₂-(2-pyridyl) |
| 138 | H | H | –CH₂CH₂CH₂CH₂– | –S–CH₂-(2-pyridyl) |
| 139 | (CH₃)₃COC(O)– | H | –CH₂CH₂CH₂CH₂– | –S–CH₂-(3-pyridyl) |
| 140 | PhCH₂OC(O)– | H | –CH₂CH₂CH₂CH₂– | –S–CH₂-(3-pyridyl) |
| 141 | H | H | –CH₂CH₂CH₂CH₂– | –S–CH₂-(3-pyridyl) |
| 142 | (CH₃)₃COC(O)– | H | –CH₂CH₂CH₂CH₂– | –S–CH₂-(4-pyridyl) |
| 143 | PhCH₂OC(O)– | H | –CH₂CH₂CH₂CH₂– | –S–CH₂-(4-pyridyl) |
| 144 | H | H | –CH₂CH₂CH₂CH₂– | –S–CH₂-(4-pyridyl) |
| 145 | (CH₃)₃COC(O)– | H | Ph | H | –S–CH₂-(2-furyl) |
| 146 | PhCH₂OC(O)– | H | Ph | H | –S–CH₂-(2-furyl) |

TABLE 1-continued
| | | | | |
|---|---|---|---|---|
| 147 | H | H | 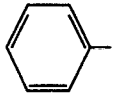 | H 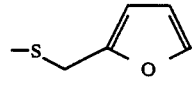 |
| 148 | (CH₃)₃COC(O)— | H | 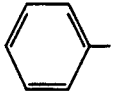 | H 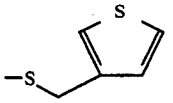 |
| 149 | PhCH₂OC(O)— | H | 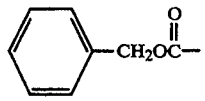 | H 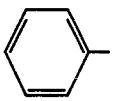 |
| 150 | H | H | 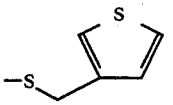 | H 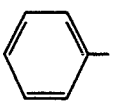 |
| 151 | (CH₃)₃COC(O)— | H | PhCH₂— | H 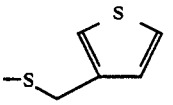 |
| 152 | (CH₃)₃COC(O)— | CH₃— | PhCH₂— | H 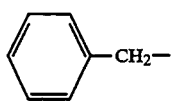 |
| 153 | (CH₃)₂CHCH₂OC(O)— | H | PhCH₂— | H 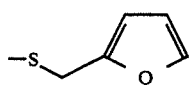 |
| 154 | CyCH₂OC(O)— | H | PhCH₂— | H 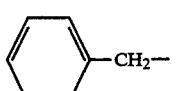 |
| 155 | PhCH₂OC(O)— | H | PhCH₂— | H 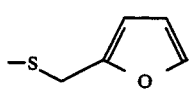 |
| 156 | PhCH₂OC(O)— | CH₃— | PhCH₂— | H 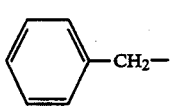 |
| 157 | 4-CH₃O-C₆H₄-CH₂OC(O)— | H | PhCH₂— | H 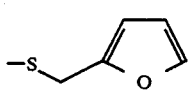 |
| 158 | 4-Cl-C₆H₄-CH₂OC(O)— | H | PhCH₂— | H 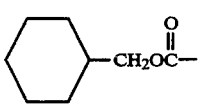 |

TABLE 1-continued

| # | R1 | R2 | R3 | R4 |
|---|---|---|---|---|
| 159 | 9,10-dihydroanthracen-9-yl-CH2OC(O)– | H | C6H5-CH2– | –S-CH2-(2-furyl) |
| 160 | (N-succinimidyl)-O-C(O)– | H | C6H5-CH2– | –S-CH2-(2-furyl) |
| 161 | H | H | C6H5-CH2– | –S-CH2-(2-furyl) |
| 162 | CH3C(O)– | H | C6H5-CH2– | –S-CH2-(2-furyl) |
| 163 | (CH3)2CHCH2C(O)– | H | C6H5-CH2– | –S-CH2-(2-furyl) |
| 164 | (CH3)2CHCH2CH2C(O)– | H | C6H5-CH2– | –S-CH2-(2-furyl) |
| 165 | C6H5-CH2C(O)– | H | C6H5-CH2– | –S-CH2-(2-furyl) |
| 166 | C6H5-CH2CH2C(O)– | H | C6H5-CH2– | –S-CH2-(2-furyl) |
| 167 | C6H5-CH2CH2CH2C(O)– | H | C6H5-CH2– | –S-CH2-(2-furyl) |
| 168 | (quinolin-8-yl)-CH2C(O)– | H | C6H5-CH2– | –S-CH2-(2-furyl) |

| | | | | | |
|---|---|---|---|---|---|
| 169 | 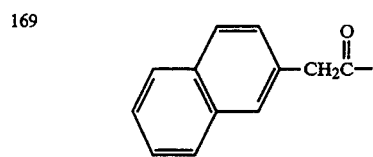 | H | 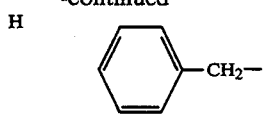 | H | 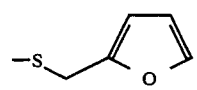 |
| 170 |  | H | 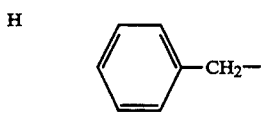 | H | 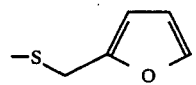 |
| 171 |  | H | 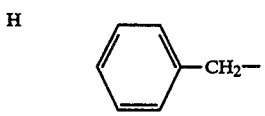 | H | 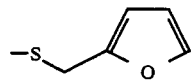 |
| 172 | 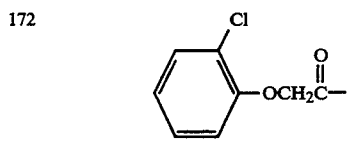 | H | 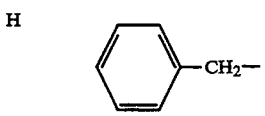 | H | 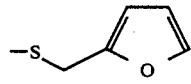 |
| 173 | 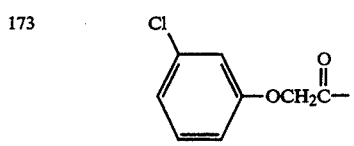 | H | 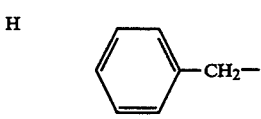 | H | 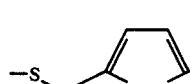 |
| 174 | 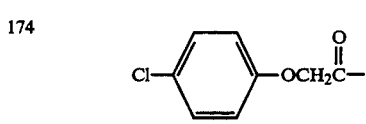 | H | 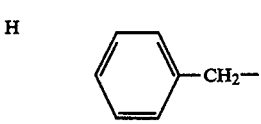 | H | 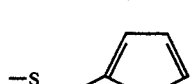 |
| 175 | 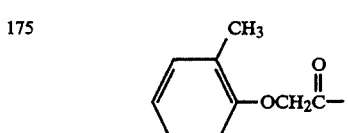 | H | 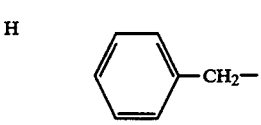 | H | 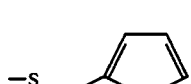 |
| 176 | 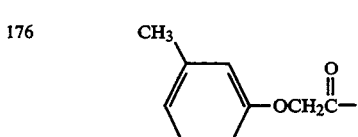 | H | 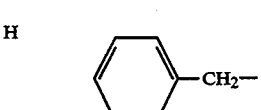 | H |  |
| 177 | 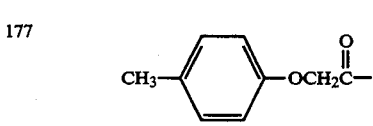 | H | 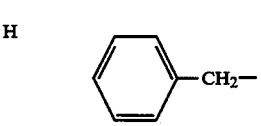 | H | 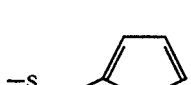 |
| 178 | 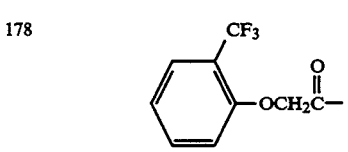 | H | 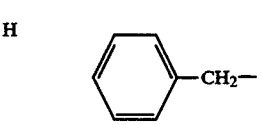 | H | 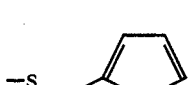 |
| 179 | 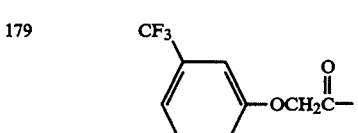 | H | 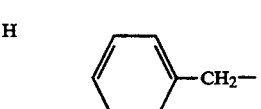 | H |  |
| 180 | 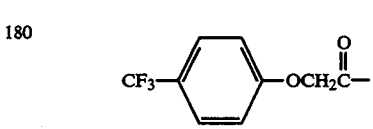 | H | 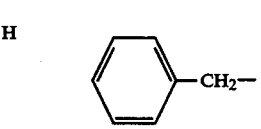 | H |  |

| # | | | | |
|---|---|---|---|---|
| 181 | 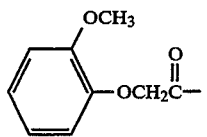 | H | 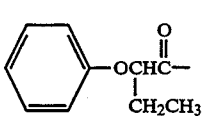 | H | 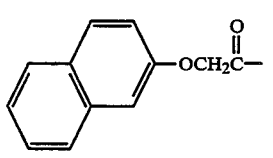 |
| 182 | 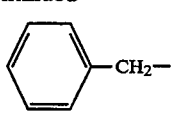 | H | 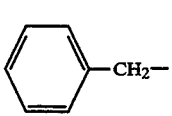 | H | 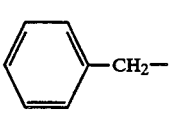 |
| 183 | 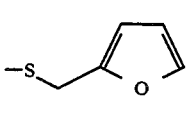 | H | 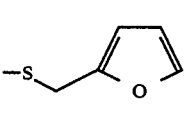 | H | 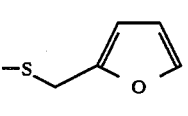 |
| 184 | 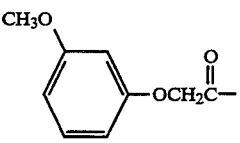 | H | 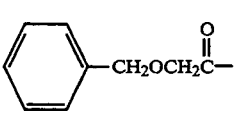 | H | 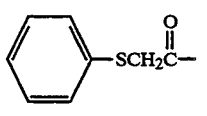 |
| 185 | 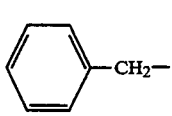 | H | 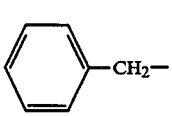 | H | 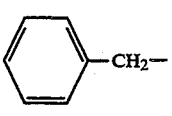 |
| 186 | 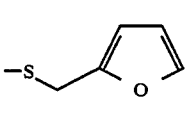 | H | 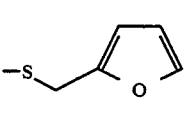 | H | 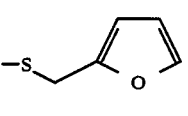 |
| 187 | 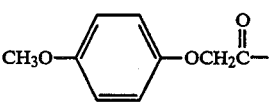 | H | 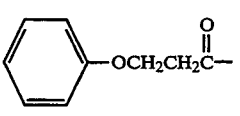 | H | 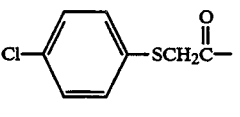 |
| 188 | 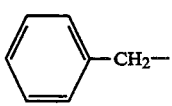 | H | 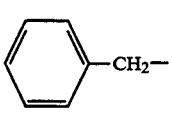 | H | 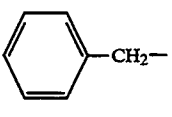 |
| 189 | 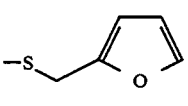 | H | 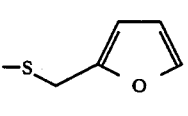 | H | 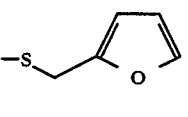 |
| 190 | 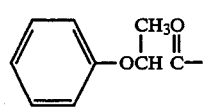 | H | 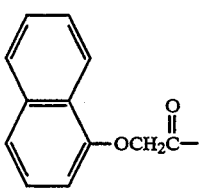 | H | 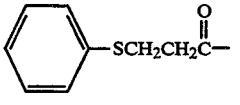 |
| 191 | 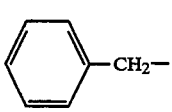 | H | 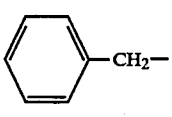 | H | 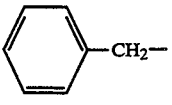 |
| 192 | 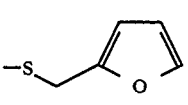 | H | 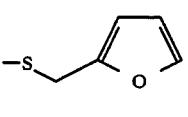 | H | 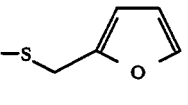 |

-continued
| | | | | | |
|---|---|---|---|---|---|
| 193 | 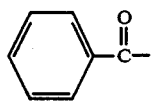 | H | 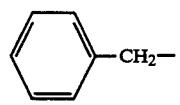 | H | 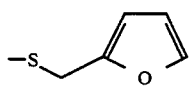 |
| 194 | 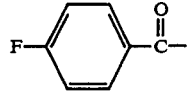 | H | 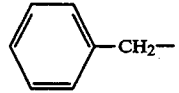 | H | 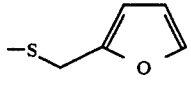 |
| 195 | 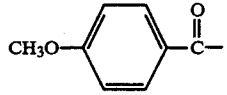 | H | 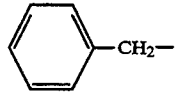 | H | 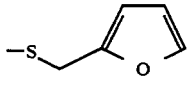 |
| 196 | 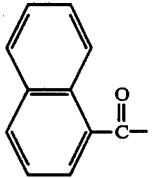 | H | 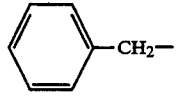 | H | 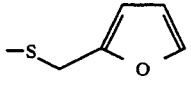 |
| 197 | 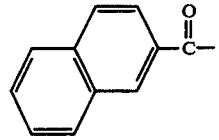 | H | 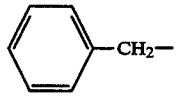 | H | 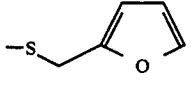 |
| 198 | 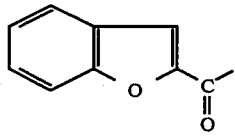 | H | 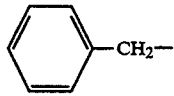 | H | 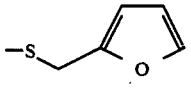 |
| 199 | 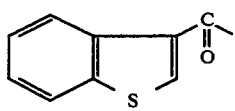 | H | 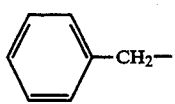 | H | 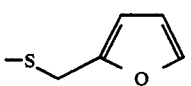 |
| 200 | 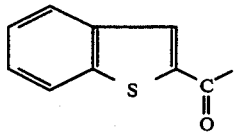 | H | 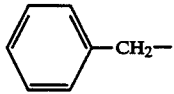 | H | 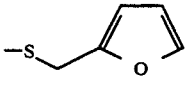 |
| 201 | 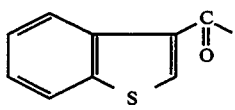 | H | 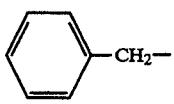 | H | 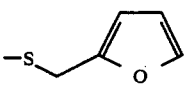 |
| 202 | 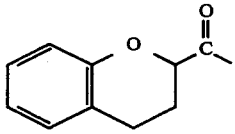 | H | 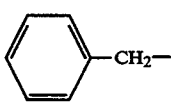 | H | 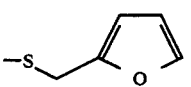 |
| 203 | 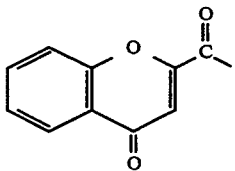 | H | 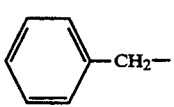 | H | 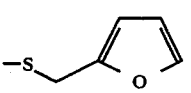 |

| | | | | |
|---|---|---|---|---|
| 204 | (CH₃)₃COC(O)- | H | PhCH₂- | H | -S-CH₂-(furan-3-yl) |
| 205 | PhCH₂OC(O)- | H | PhCH₂- | H | -S-CH₂-(furan-3-yl) |
| 206 | H | H | PhCH₂- | H | -S-CH₂-(furan-3-yl) |
| 207 | (CH₃)₃COC(O)- | H | PhCH₂- | H | -S-CH₂-(thiophen-2-yl) |
| 208 | PhCH₂OC(O)- | H | PhCH₂- | H | -S-CH₂-(thiophen-2-yl) |
| 209 | H | H | PhCH₂- | H | -S-CH₂-(thiophen-2-yl) |
| 210 | (CH₃)₃COC(O)- | H | PhCH₂- | H | -S-CH₂-(thiophen-3-yl) |
| 211 | PhCH₂OC(O)- | H | PhCH₂- | H | -S-CH₂-(thiophen-3-yl) |
| 212 | 4-CH₃O-C₆H₄-CH₂OC(O)- | H | PhCH₂- | H | -S-CH₂-(thiophen-3-yl) |
| 213 | H | H | PhCH₂- | H | -S-CH₂-(thiophen-3-yl) |
| 214 | PhSCH₂OC(O)- | H | PhCH₂- | H | -S-CH₂-(thiophen-3-yl) |
| 215 | 2-CH₃O-C₆H₄-OCH₂OC(O)- | H | PhCH₂- | H | -S-CH₂-(thiophen-3-yl) |
| 216 | 3-CH₃O-C₆H₄-OCH₂OC(O)- | H | PhCH₂- | H | -S-CH₂-(thiophen-3-yl) |

-continued
| | | | | | |
|---|---|---|---|---|---|
| 217 | 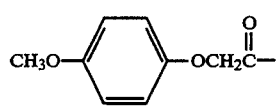 | H | 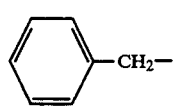 | H | 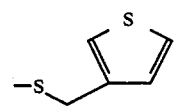 |
| 218 | 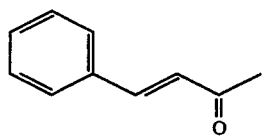 | H | 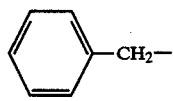 | H | 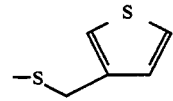 |
| 219 | 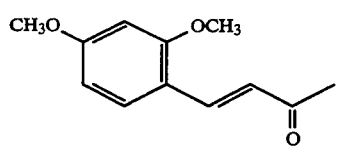 | H | 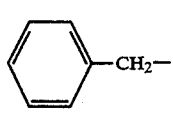 | H | 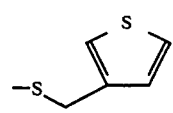 |
| 220 | 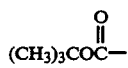 | H | 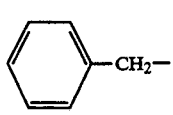 | H | 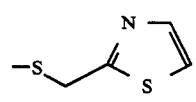 |
| 221 | 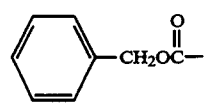 | H | 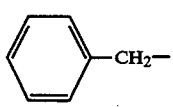 | H | 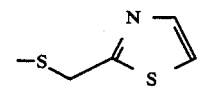 |
| 222 | H | H | 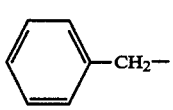 | H | 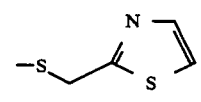 |
| 223 | 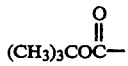 | H | 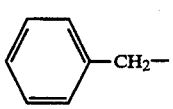 | H | 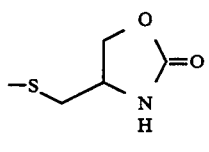 |
| 224 | 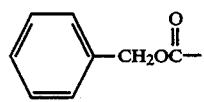 | H | 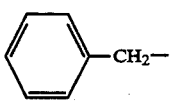 | H | 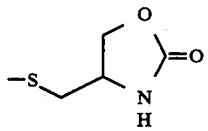 |
| 225 | H | H | 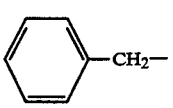 | H | 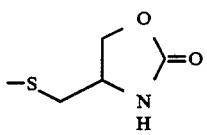 |
| 226 |  | H | 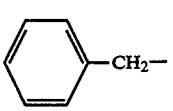 | H | 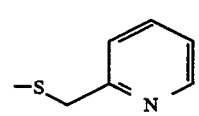 |
| 227 | 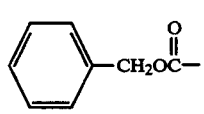 | H | 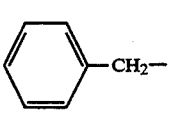 | H | 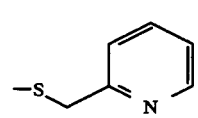 |
| 228 | H | H | 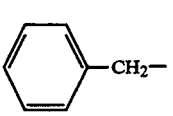 | H | 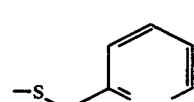 |

| # | | | | | |
|---|---|---|---|---|---|
| 229 | (CH₃)₃COC(=O)– | H | C₆H₅-CH₂– | H | –S-CH₂-(3-pyridyl) |
| 230 | C₆H₅-CH₂-OC(=O)– | H | C₆H₅-CH₂– | H | –S-CH₂-(3-pyridyl) |
| 231 | H | H | C₆H₅-CH₂– | H | –S-CH₂-(3-pyridyl) |
| 232 | (CH₃)₃COC(=O)– | H | C₆H₅-CH₂– | H | –S-CH₂-(4-pyridyl) |
| 233 | C₆H₅-CH₂-OC(=O)– | H | C₆H₅-CH₂– | H | –S-CH₂-(4-pyridyl) |
| 234 | H | H | C₆H₅-CH₂– | H | –S-CH₂-(4-pyridyl) |
| 235 | (CH₃)₃COC(=O)– | H | 2-F-C₆H₄-CH₂– | H | –S-CH₂-(2-furyl) |
| 236 | C₆H₅-CH₂-OC(=O)– | H | 2-F-C₆H₄-CH₂– | H | –S-CH₂-(2-furyl) |
| 237 | H | H | 2-F-C₆H₄-CH₂– | H | –S-CH₂-(2-furyl) |
| 238 | (CH₃)₃COC(=O)– | H | 2-F-C₆H₄-CH₂– | H | –S-CH₂-(3-thienyl) |
| 239 | C₆H₅-CH₂-OC(=O)– | H | 2-F-C₆H₄-CH₂– | H | –S-CH₂-(3-thienyl) |
| 240 | H | H | 2-F-C₆H₄-CH₂– | H | –S-CH₂-(3-thienyl) |

-continued
| | | | | | |
|---|---|---|---|---|---|
| 241 |  | H | 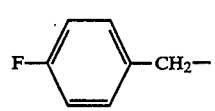 | H | 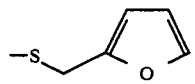 |
| 242 | 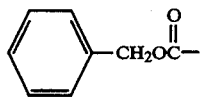 | H | 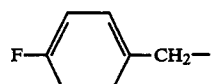 | H | 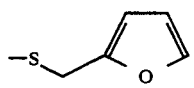 |
| 243 | H | H | 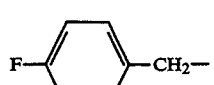 | H | 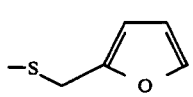 |
| 244 |  | H | 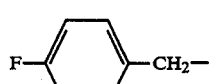 | H | 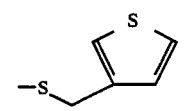 |
| 245 | 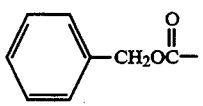 | H | 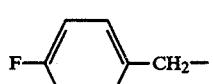 | H | 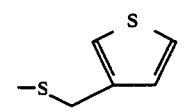 |
| 246 | H | H | 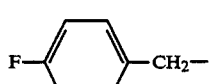 | H | 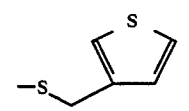 |
| 247 |  | H | 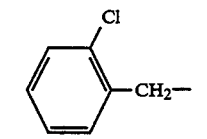 | H | 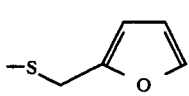 |
| 248 | 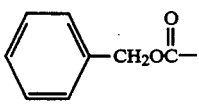 | H | 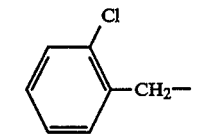 | H | 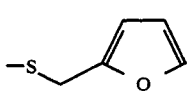 |
| 249 | H | H | 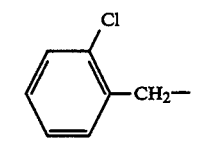 | H | 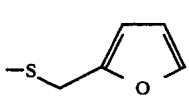 |
| 250 |  | H | 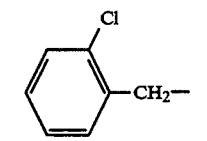 | H |  |
| 251 | 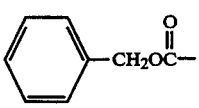 | H | 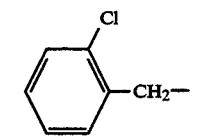 | H | 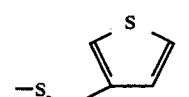 |
| 252 | H | H | 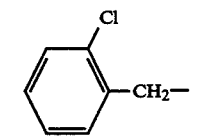 | H | 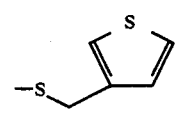 |

-continued
| | | | | | |
|---|---|---|---|---|---|
| 253 |  | H | 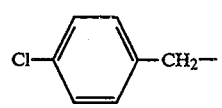 | H | 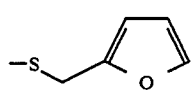 |
| 254 | 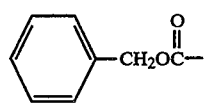 | H | 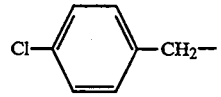 | H | 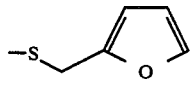 |
| 255 | H | H | 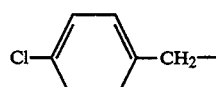 | H | 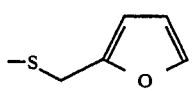 |
| 256 | 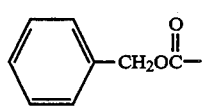 | H | 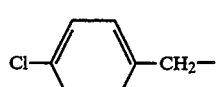 | H | 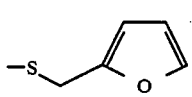 |
| 257 | 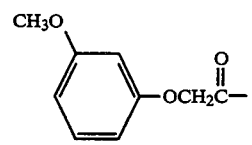 | H | 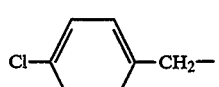 | H | 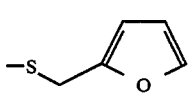 |
| 258 |  | H | 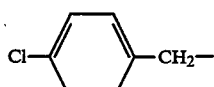 | H | 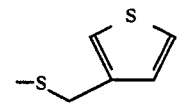 |
| 259 | 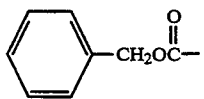 | H | 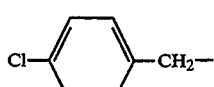 | H | 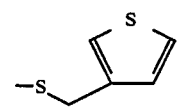 |
| 260 | H | H | 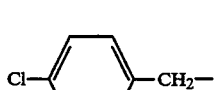 | H | 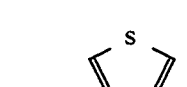 |
| 261 | 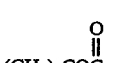 | H | 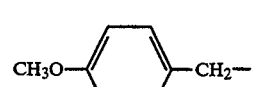 | H | 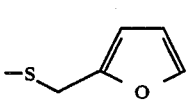 |
| 262 | 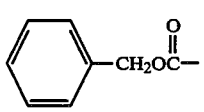 | H | 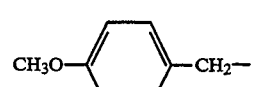 | H | 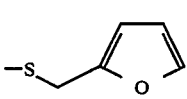 |
| 263 | H | H | 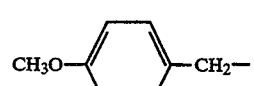 | H | 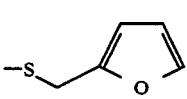 |
| 264 |  | H | 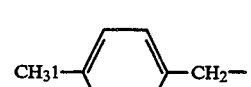 | H | 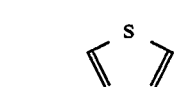 |
| 265 | 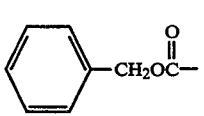 | H | 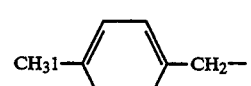 | H | 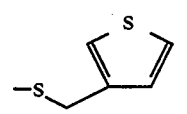 |

-continued

| | | | | | |
|---|---|---|---|---|---|
| 266 | H | H | 4-CH₃O-C₆H₄-CH₂- | H | -S-CH₂-(3-thienyl) |
| 267 | (CH₃)₃C-C(O)- | H | 4-HO-C₆H₄-CH₂- | H | -S-CH₂-(2-furyl) |
| 268 | C₆H₅-CH₂-C(O)- | H | 4-HO-C₆H₄-CH₂- | H | -S-CH₂-(2-furyl) |
| 269 | H | H | 4-HO-C₆H₄-CH₂- | H | -S-CH₂-(2-furyl) |
| 270 | (CH₃)₃C-C(O)- | H | 4-HO-C₆H₄-CH₂- | H | -S-CH₂-(3-thienyl) |
| 271 | C₆H₅-CH₂-C(O)- | H | 4-HO-C₆H₄-CH₂- | H | -S-CH₂-(3-thienyl) |
| 272 | H | H | 4-HO-C₆H₄-CH₂- | H | -S-CH₂-(3-thienyl) |
| 273 | (CH₃)₃C-C(O)- | H | C₆H₅-CH₂CH₂- | H | -S-CH₂-(2-furyl) |
| 274 | C₆H₅-CH₂-C(O)- | H | C₆H₅-CH₂CH₂- | H | -S-CH₂-(2-furyl) |
| 275 | 4-CH₃O-C₆H₄-CH₂-C(O)- | H | C₆H₅-CH₂CH₂- | H | -S-CH₂-(2-furyl) |
| 276 | H | H | C₆H₅-CH₂CH₂- | H | -S-CH₂-(2-furyl) |
| 277 | C₆H₅-CH₂-C(O)- | H | C₆H₅-CH₂CH₂- | H | -S-CH₂-(2-furyl) |
| 278 | 3-CH₃O-C₆H₄-O-CH₂-C(O)- | H | C₆H₅-CH₂CH₂- | H | -S-CH₂-(2-furyl) |

| | | | | | |
|---|---|---|---|---|---|
| 279 | 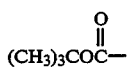 | H | 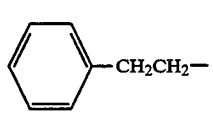 | H | 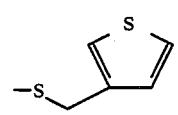 |
| 280 | 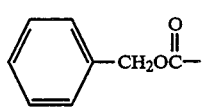 | H | 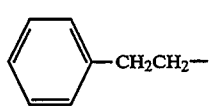 | H | 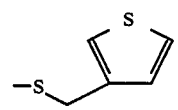 |
| 281 | H | H | 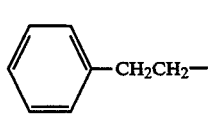 | H | 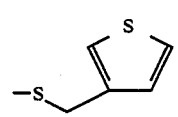 |
| 282 | 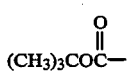 | H | 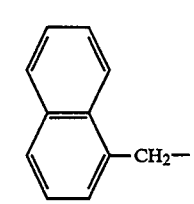 | H | 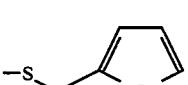 |
| 283 | 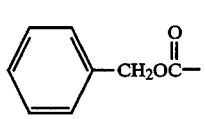 | H | 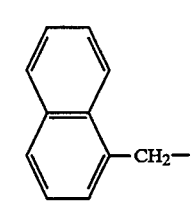 | H | 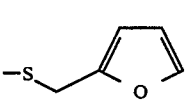 |
| 284 | H | H | 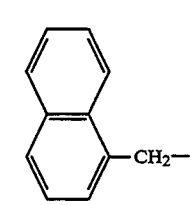 | H | 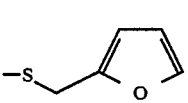 |
| 285 | 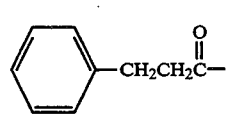 | H | 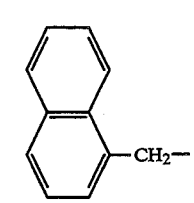 | H | 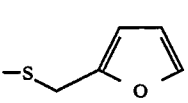 |
| 286 | 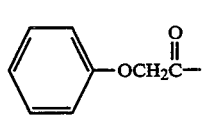 | H | 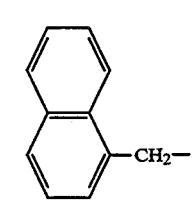 | H | 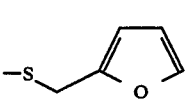 |
| 287 |  | H | 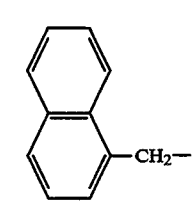 | H | 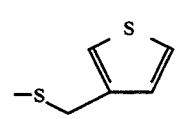 |

-continued
| | | | | | |
|---|---|---|---|---|---|
| 288 | 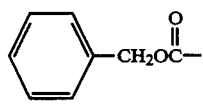 | H | 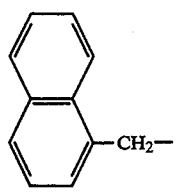 | H | 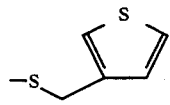 |
| 289 | H | H | 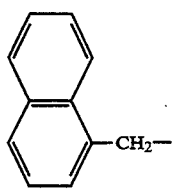 | H | 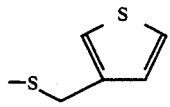 |
| 290 | 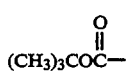 | H | 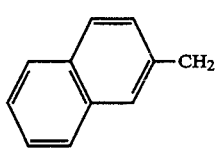 | H | 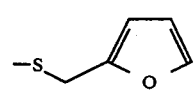 |
| 291 |  | H | 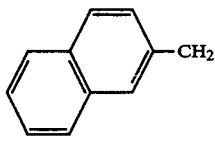 | H | 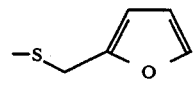 |
| 292 | 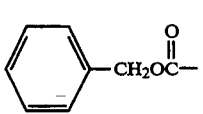 | H | 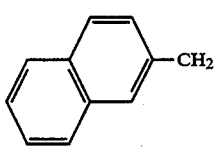 | H | 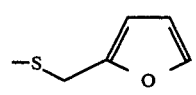 |
| 293 | H | H | 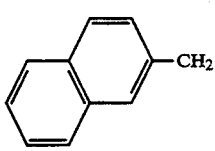 | H | 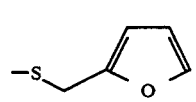 |
| 294 | 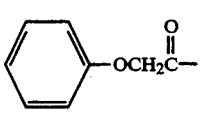 | H | 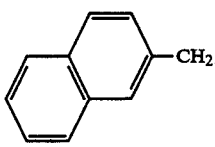 | H | 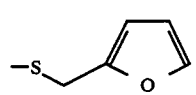 |
| 295 |  | H | 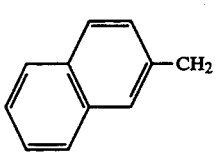 | H | 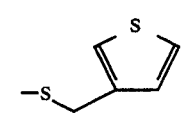 |
| 296 | 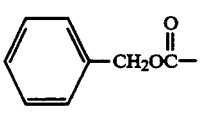 | H | 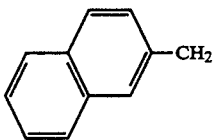 | H | 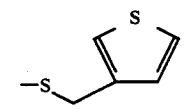 |
| 297 | H | H | 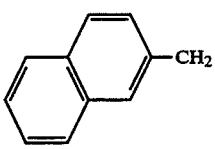 | H | 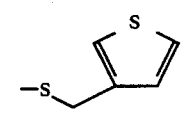 |

-continued

| | | | | | |
|---|---|---|---|---|---|
| 298 | (CH₃)₃COC(O)— | H | CH₃CH₂CH₂CH₂— | H | —OCH₂-(2-furyl) |
| 299 | PhCH₂OC(O)— | H | CH₃CH₂CH₂CH₂— | H | —OCH₂-(2-furyl) |
| 300 | H | H | CH₃CH₂CH₂CH₂— | H | —OCH₂-(2-furyl) |
| 301 | (CH₃)₃COC(O)— | H | CH₃CH₂CH₂CH₂— | H | —S-CH₂-(3-thienyl) |
| 302 | PhCH₂OC(O)— | H | CH₃CH₂CH₂CH₂— | H | —OCH₂-(3-furyl) |
| 303 | H | H | CH₃CH₂CH₂CH₂— | H | —OCH₂-(3-furyl) |
| 304 | (CH₃)₃COC(O)— | H | CH₃CH₂CH₂CH₂— | H | —OCH₂-(2-thienyl) |
| 305 | PhCH₂OC(O)— | H | CH₃CH₂CH₂CH₂— | H | —OCH₂-(2-thienyl) |
| 306 | H | H | CH₃CH₂CH₂CH₂— | H | —OCH₂-(2-thienyl) |
| 307 | (CH₃)₃COC(O)— | H | CH₃CH₂CH₂CH₂— | H | —OCH₂-(3-thienyl) |
| 308 | PhCH₂OC(O)— | H | CH₃CH₂CH₂CH₂— | H | —OCH₂-(3-thienyl) |
| 309 | H | H | CH₃CH₂CH₂CH₂— | H | —OCH₂-(3-thienyl) |
| 310 | (CH₃)₃COC(O)— | H | CH₃CH₂CH₂CH₂— | H | —OCH₂CH₂-(2-furyl) |
| 311 | PhCH₂OC(O)— | H | CH₃CH₂CH₂CH₂— | H | —OCH₂CH₂-(2-furyl) |

5,424,325
-continued
| | | | | | |
|---|---|---|---|---|---|
| 312 | H | H | CH₃CH₂CH₂CH₂— | H | 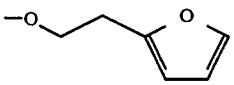 |
| 313 | (CH₃)₃COC(O)— | H | CH₃CH₂CH₂CH₂— | H | 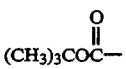 |
| 314 | C₆H₅CH₂OC(O)— | H | CH₃CH₂CH₂CH₂— | H | 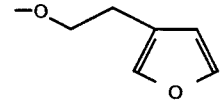 |
| 315 | H | H | CH₃CH₂CH₂— | H | 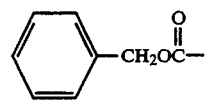 |
| 316 | (CH₃)₃COC(O)— | H | C₆H₅CH₂— | H | 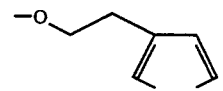 |
| 317 | C₆H₅CH₂OC(O)— | H | C₆H₅CH₂— | H | 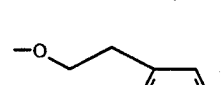 |
| 318 | 4-CH₃O-C₆H₄CH₂OC(O)— | H | C₆H₅CH₂— | H | 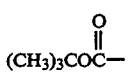 |
| 319 | H | H | C₆H₅CH₂— | H | 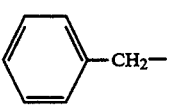 |
| 320 | C₆H₅OCH₂C(O)— | H | C₆H₅CH₂— | H | 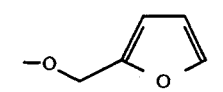 |
| 321 | 3-CH₃O-C₆H₄OCH₂C(O)— | H | C₆H₅CH₂— | H | 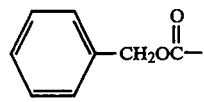 |
| 322 | (CH₃)₃COC(O)— | H | C₆H₅CH₂— | H | 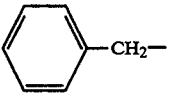 |
| 323 | C₆H₅CH₂OC(O)— | H | C₆H₅CH₂— | H | 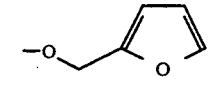 |
| 324 | H | H | C₆H₅CH₂— | H | 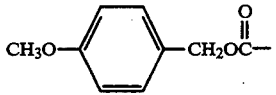 |

| | | | | | |
|---|---|---|---|---|---|
| 338 |  | H |  | H | 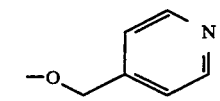 |
| 339 | 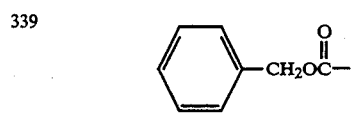 | H | 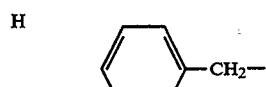 | H | 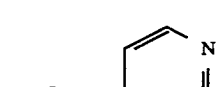 |
| 340 | H | H | 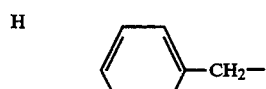 | H | 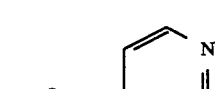 |
| 341 |  | H | 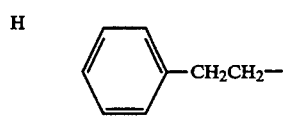 | H | 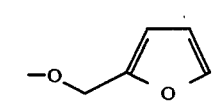 |
| 342 | 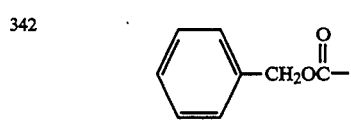 | H | 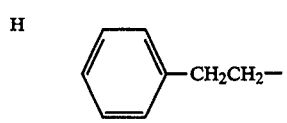 | H | 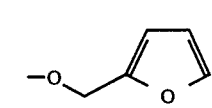 |
| 343 | H | H | 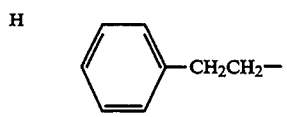 | H | 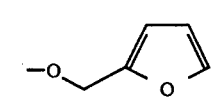 |
| 344 | 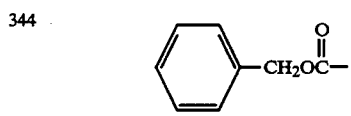 | H | 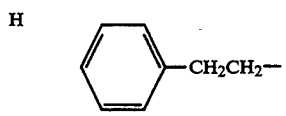 | H | |
| 345 | 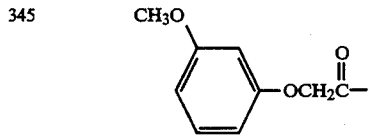 | H | 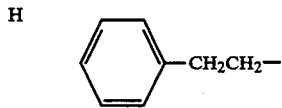 | H | 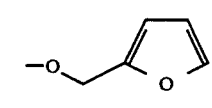 |
| 346 |  | H | CH₃— | CH₃— | 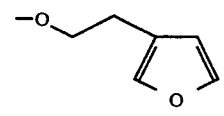 |
| 347 | 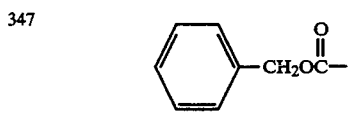 | H | CH₃— | CH₃— | 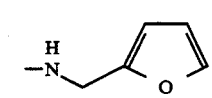 |
| 348 | H | H | CH₃— | CH₃— | 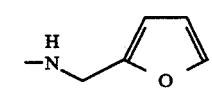 |
| 349 |  | H | CH₃— | CH₃— | 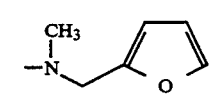 |
| 350 | 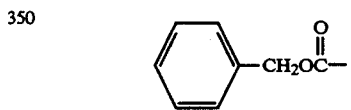 | H | CH₃— | CH₃— | 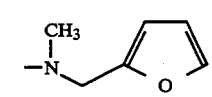 |
| 351 | H | H | H | CH₃— | |

-continued
| | | | | | |
|---|---|---|---|---|---|
| 352 |  | H | CH₃CH₂CH₂— | H | 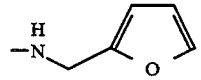 |
| 353 |  | H | CH₃CH₂CH₂— | H | 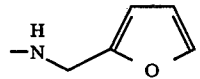 |
| 354 | H | H | CH₃CH₂CH₂— | H | 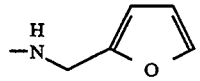 |
| 355 |  | H | CH₃CH₂CH₂— | H | 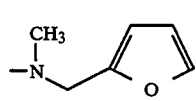 |
| 356 |  | H | CH₃CH₂CH₂— | H | 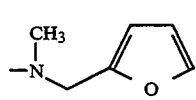 |
| 357 | 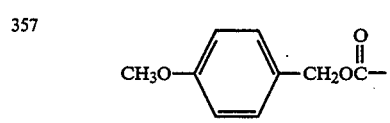 | H | CH₃CH₂CH₂— | H | 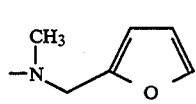 |
| 358 | H | H | CH₃CH₂CH₂— | H | 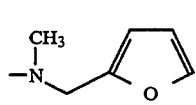 |
| 359 | 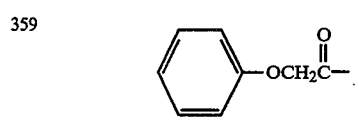 | H | CH₃CH₂CH₂— | H | 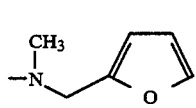 |
| 360 | 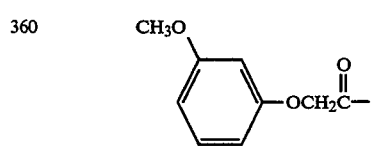 | H | CH₃CH₂CH₂— | H | 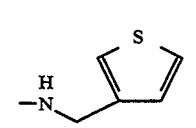 |
| 361 |  | H | CH₃CH₂CH₂— | H | 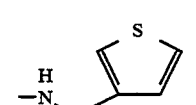 |
| 362 | 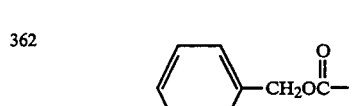 | H | CH₃CH₂CH₂— | H | 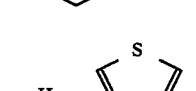 |
| 363 | H | H | CH₃CH₂CH₂— | H | 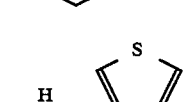 |
| 364 |  | H | CH₃CH₂CH₂— | H | 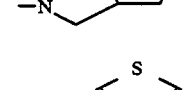 |
| 365 | 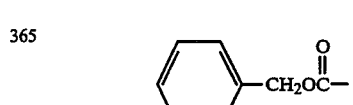 | H | CH₃CH₂CH₂— | H | 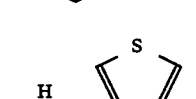 |

-continued
| | | | | | |
|---|---|---|---|---|---|
| 366 | H | H | CH₃CH₂CH₂— | H | 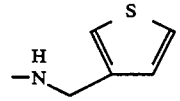 |
| 367 | (CH₃)₃COC(O)— | H | —CH₂CH₂CH₂CH₂CH₂— | | 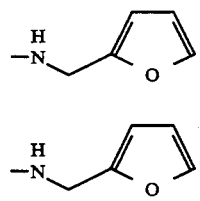 |
| 368 | 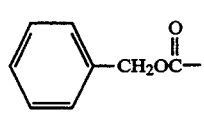 | H | —CH₂CH₂CH₂CH₂CH₂— | | 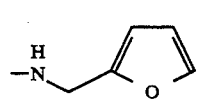 |
| 369 | H | H | —CH₂CH₂CH₂CH₂CH₂— | | 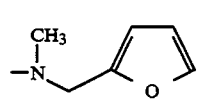 |
| 370 | (CH₃)₃COC(O)— | H | —CH₂CH₂CH₂CH₂CH₂— | | 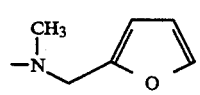 |
| 371 | 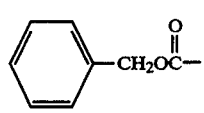 | H | —CH₂CH₂CH₂CH₂CH₂— | | 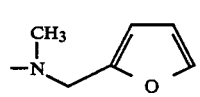 |
| 372 | H | H | —CH₂CH₂CH₂CH₂CH₂— | | 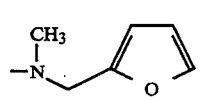 |
| 373 | 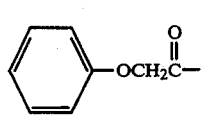 | H | —CH₂CH₂CH₂CH₂CH₂— | | 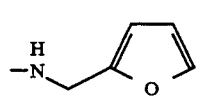 |
| 374 | (CH₃)₃COC(O)— | H | 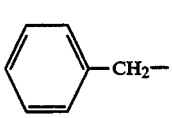 | H | 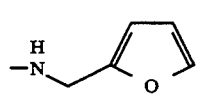 |
| 375 | 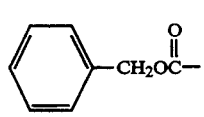 | H | 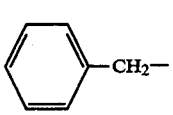 | H | 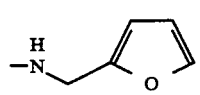 |
| 376 | H | H | 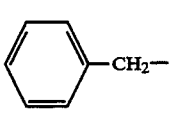 | H | 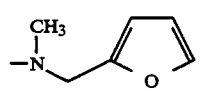 |
| 377 | (CH₃)₃COC(O)— | H | 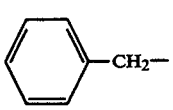 | H | 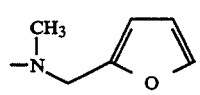 |
| 378 | 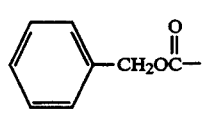 | H | 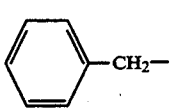 | H | 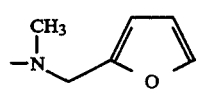 |
| 379 | 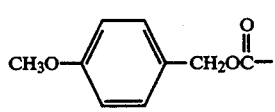 | H | 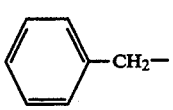 | H | |

-continued
| # | | | | | |
|---|---|---|---|---|---|
| 380 | H | H | 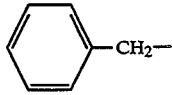 | H | 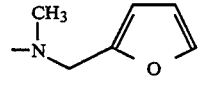 |
| 381 | 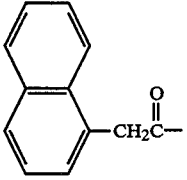 | H | 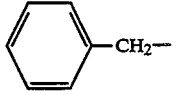 | H | 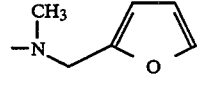 |
| 382 | 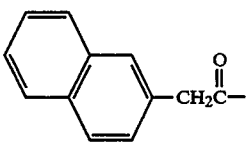 | H | 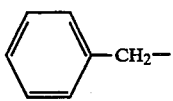 | H | 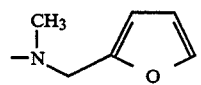 |
| 383 | 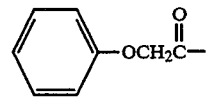 | H | 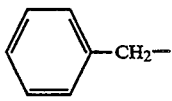 | H | 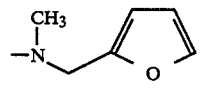 |
| 384 | 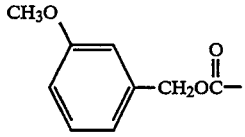 | H | 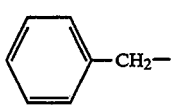 | H | 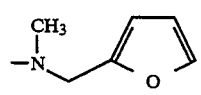 |
| 385 | $(CH_3)_3CO\overset{O}{\underset{\|}{C}}-$ | H | 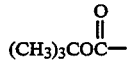 | H | 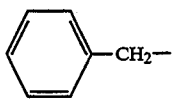 |
| 386 | 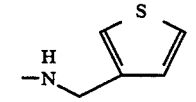 | H | 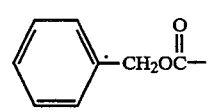 | H | 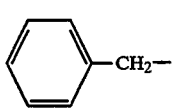 |
| 387 | H | H | 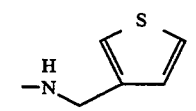 | H | 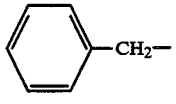 |
| 388 | $(CH_3)_3CO\overset{O}{\underset{\|}{C}}-$ | H | 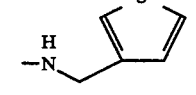 | H |  |
| 389 | 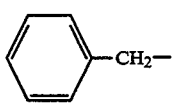 | H | 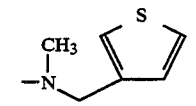 | H | 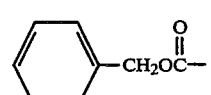 |
| 390 | H | H | 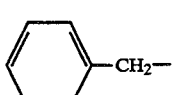 | H | 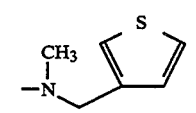 |
| 391 | 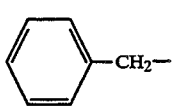 | H | 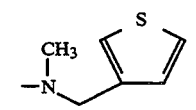 | H | 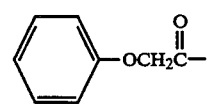 |

-continued
| | | | | | |
|---|---|---|---|---|---|
| 392 | 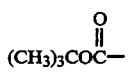 | H | 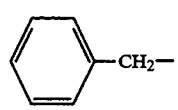 | H | 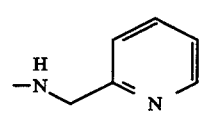 |
| 393 | 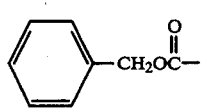 | H | 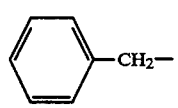 | H | 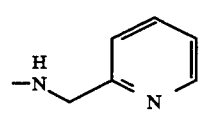 |
| 394 | H | H | 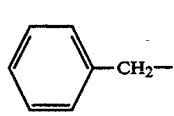 | H | 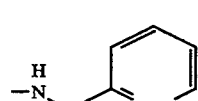 |
| 395 |  | H | 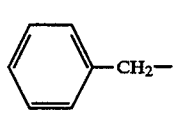 | H | 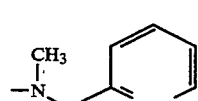 |
| 396 | 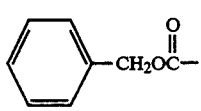 | H | 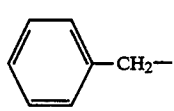 | H | 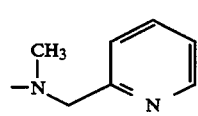 |
| 397 | H | H | 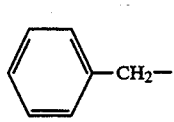 | H | 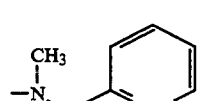 |
| 398 |  | H | 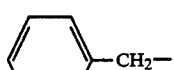 | H | 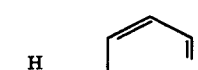 |
| 399 | 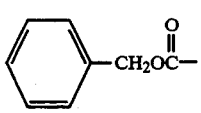 | H | 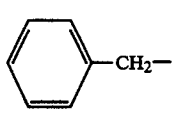 | H | 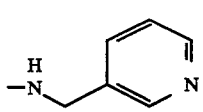 |
| 400 | 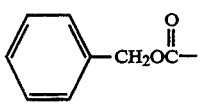 | H | 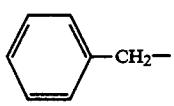 | H | 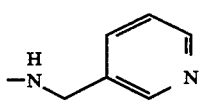 |
| 401 |  | H | 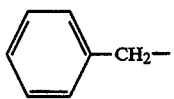 | H | 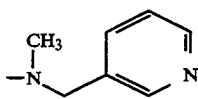 |
| 402 | 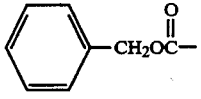 | H | 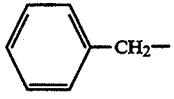 | H | 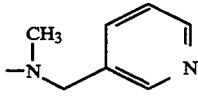 |
| 403 | H | H | 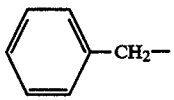 | H | 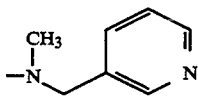 |
| 404 | 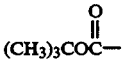 | H | 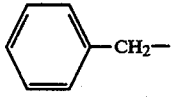 | H | 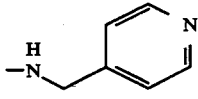 |

| # | | | | |
|---|---|---|---|---|
| 405 | PhCH2OC(O)- | H | PhCH2- | H, -NHCH2-(4-pyridyl) |
| 406 | H | H | PhCH2- | H, -NHCH2-(4-pyridyl) |
| 407 | (CH3)3COC(O)- | H | PhCH2- | CH3, -N(CH3)CH2-(4-pyridyl) |
| 408 | PhCH2OC(O)- | H | PhCH2- | CH3, -N(CH3)CH2-(4-pyridyl) |
| 409 | H | H | PhCH2- | CH3, -N(CH3)CH2-(4-pyridyl) |
| 410 | (CH3)3COC(O)- | H | PhCH2CH2- | H, -NHCH2-(2-furyl) |
| 411 | PhCH2OC(O)- | H | PhCH2CH2- | H, -NHCH2-(2-furyl) |
| 412 | H | H | PhCH2CH2- | H, -NHCH2-(2-furyl) |
| 413 | (CH3)3COC(O)- | H | PhCH2CH2- | CH3, -N(CH3)CH2-(2-furyl) |
| 414 | PhCH2OC(O)- | H | PhCH2CH2- | CH3, -N(CH3)CH2-(2-furyl) |
| 415 | H | H | PhCH2CH2- | CH3, -N(CH3)CH2-(2-furyl) |
| 416 | PhOCH2C(O)- | H | PhCH2CH2- | CH3, -N(CH3)CH2-(2-furyl) |
| 417 | 3-CH3O-C6H4-OCH2C(O)- | H | PhCH2CH2- | CH3, -N(CH3)CH2-(2-furyl) |

| | | | | | |
|---|---|---|---|---|---|
| 418 |  | H | 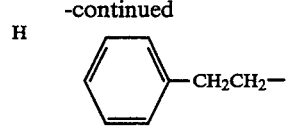 | H | 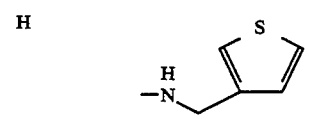 |
| 419 | 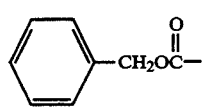 | H | 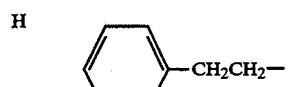 | H | 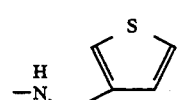 |
| 420 | H | H | 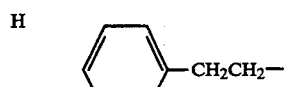 | H | 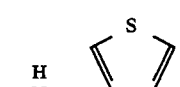 |
| 421 |  | H | 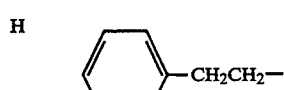 | H | 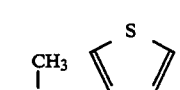 |
| 422 | 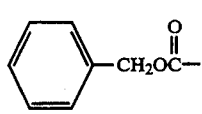 | H | 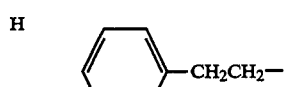 | H | 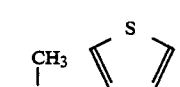 |
| 423 | H | H | 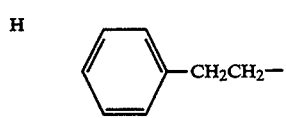 | H | 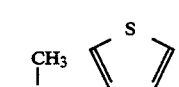 |
| 424 | 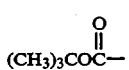 | H |  | H | 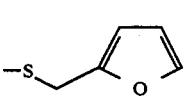 |
| 425 | 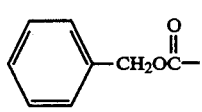 | H |  | H | 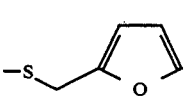 |
| 426 | H | H |  | H | 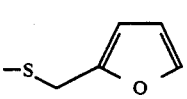 |
| 427 |  | H | 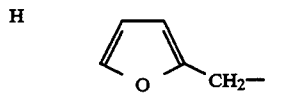 | H | 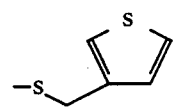 |
| 428 | 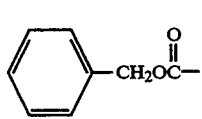 | H |  | H | 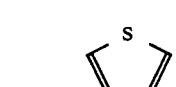 |
| 429 | H | H | 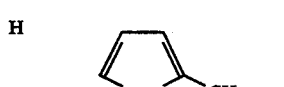 | H | 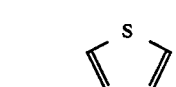 |
| 430 |  | H | 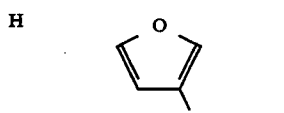 | H | 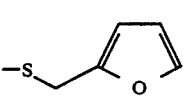 |
| 431 | 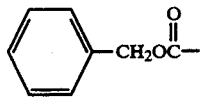 | H | 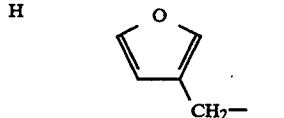 | H | 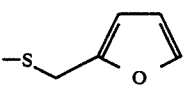 |

| | | | | | |
|---|---|---|---|---|---|
| 432 | H | H | 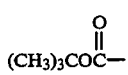 | H | 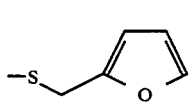 |
| 433 | 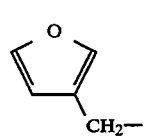 | H | 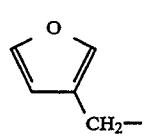 | H | 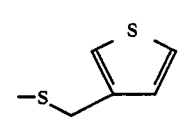 |
| 434 | 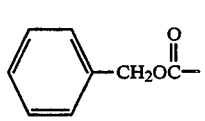 | H | 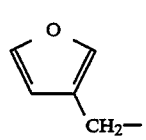 | H | 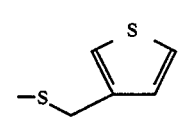 |
| 435 | H | H | 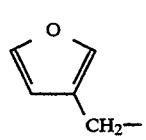 | H | 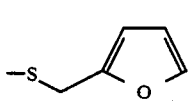 |
| 436 | 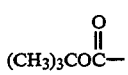 | H | 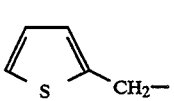 | H | 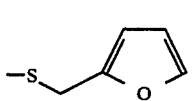 |
| 437 | 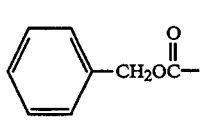 | H | 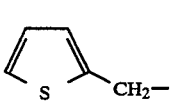 | H | 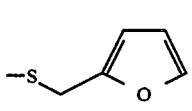 |
| 438 | H | H | 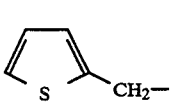 | H | 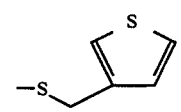 |
| 439 | 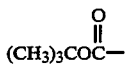 | H | 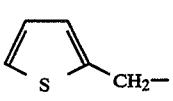 | H | 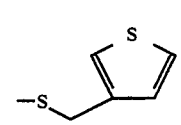 |
| 440 | 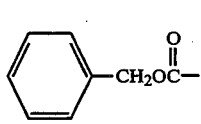 | H | 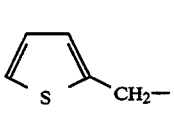 | H | 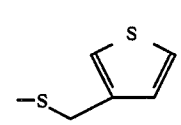 |
| 441 | H | H | 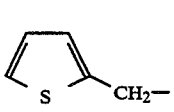 | H | 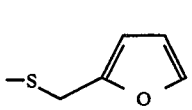 |
| 442 |  | H | 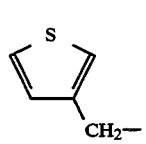 | H | 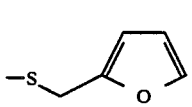 |
| 443 | 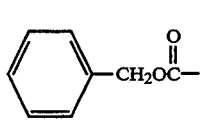 | H | 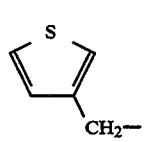 | H | 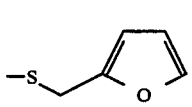 |
| 444 | H | H | 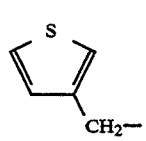 | H | |

| 445 | 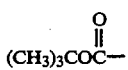 | H | 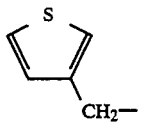 | H | 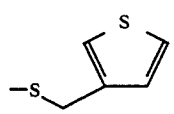 |
| 446 | 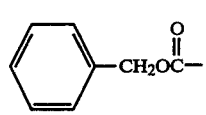 | H | 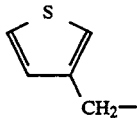 | H | 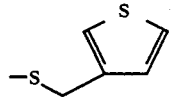 |
| 447 | H | H | 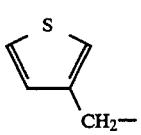 | H | 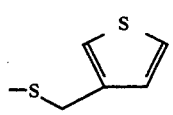 |

A method of preparing the compound according to the present invention is now described. The aminoketone derivatives having the aforementioned formula (I) may be prepared through, but not limited to, the following procedures.

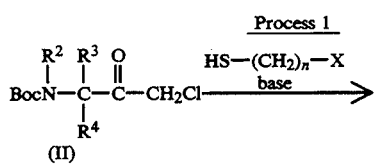

In the above formulae, $R^2$, $R^3$, $R^4$, n and X are as hereinabove defined while Boc is a tert-butoxycarbonyl group.

Chloromethyl ketone derivatives having the formula (II) can be readily synthesized using a known method disclosed in Chemical and Pharmaceutical Bulletin, vol. 37, page 3108, 1989. Thiomethyl ketone derivatives having the formula (III) can be produced by means of dissolving such chloromethyl ketone derivatives in a solvent, e.g., diethyl ether, tetrahydrofuran, dioxane, ethyl acetate, methylene chloride or chloroform, and reacting therewith mercaptan having the formula HS—$(CH_2)_n$—X in the presence of a base. The exemplified base applicable includes sodium hydroxide, potassium hydroxide, sodium hydride, triethylamine and pyridine.

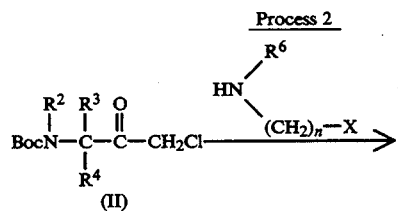

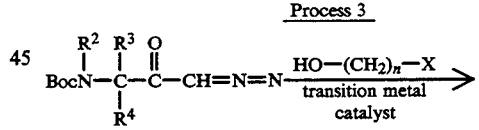

In the above formulae, Boc, $R^2$, $R^3$, $R^4$, $R^6$, n and X are as hereinabove defined.

Diaminoketone derivatives having the formula (IV) can be produced by means of dissolving the chloromethyl ketone derivatives having the formula (II) in a solvent, e.g., diethyl ether, tetrahydrofuran, dioxane, ethyl acetate, chloroform or methylene chloride, and reacting therewith amine having the formula:

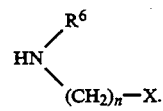

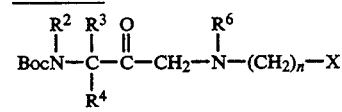

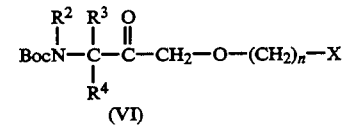

In the above formulae, Boc, $R^2$, $R^3$, $R^4$, n and X are as hereinabove defined.

Diazomethyl ketone having the formula (V) can be readily prepared using a known method disclosed in Methods in Enzymology, vol. 80, page 802, 1981. Oxymethyl ketone derivatives having the formula (VI) can be produced by means of dissolving the diazomethyl ketone in a solvent such as chloroform or methylene chloride and reacting therewith alcohol having the formula HO—$(CH_2)_n$—X in the presence of a transition metal catalyst including CuO, $Rh_2(OAc)_4$ and so on. In this event, the compound having the formula (V) may be dissolved directly in the alcohol, HO—(CH$_2$)$_n$—X, to advance the reaction without using the solvent such as chloroform or methylene chloride.

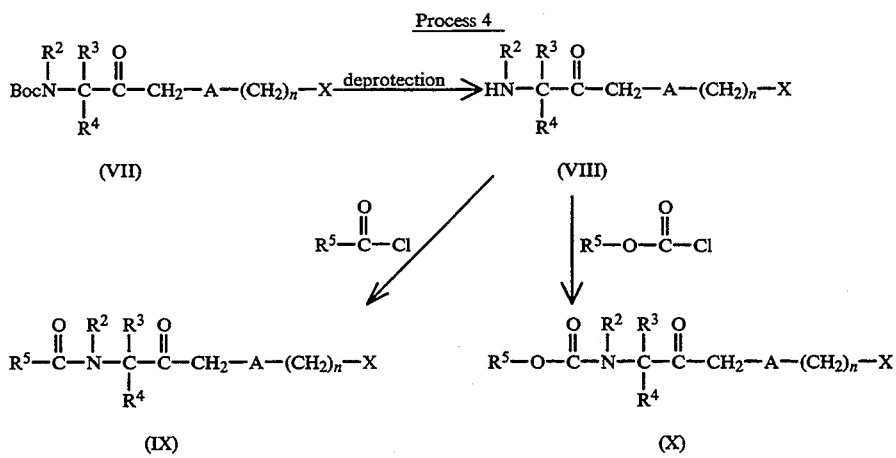

In the above formulae, Boc, R$^2$, R$^3$, R$^4$, R$^5$, A, n and X are as hereinabove defined.

The compound having the formula (VII), which is prepared according to any one of processes 1 through 3, has a Boc group. Deprotection of this Boc group under the ordinary reaction conditions results in production of amine having the formula (VIII) or a salt of the amine. The deprotection can be made with, but not limited to, a hydrochloric acid solution, hydrochloric acid-ethanol, hydrogen chloride-ethyl acetate, hydrogen chloride-dioxane, hydrobromic acid and hydrogen bromide-acetic acid. In addition, the compound having the formula (IX) is produced by means of dissolving the compound (VIII) in an ordinary organic solvent such as chloroform, methylene chloride, ethyl acetate and dimethylformamide and reacting therewith acylchloride having the formula:

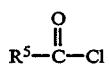

in the presence of amine such as triethylamine or pyridine. Likewise, the compound having the formula (X) is produced by means of reaction chloroformic derivatives having the formula:

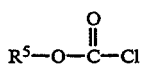

with the compound having the formula (VIII).

It may become necessary to protect or deprotect functional groups of each compound produced during the sequence of operations in the above mentioned processes 1 through 4. Such protection or deprotection can be achieved readily with a common technique ordinarily used in organic synthetic reactions.

For applying the compound according to the present invention to the clinical fields, the ratio of the therapeutically active component relative to the carrier can be altered within the range between 1% to 99% by weight. For example, the compound according to the present invention may be formed into various dosage forms for oral administration. Such dosage forms include granules, fine granules, powders, tablets, hard gelatin capsules, soft elastic capsules, syrup, emulsion, suspension and liquid preparation. Alternatively, the compound may be used as parenteral injections for intravenous, intramuscular or subcutaneous injections. It may also be used as a suppository. In addition, the compound may be formed into powders for injection and prepared whenever it becomes necessary. The drug according to the present invention can be prepared with adequate organic or inorganic medical diluent and/or solid or liquid carrier suitable for oral, rectal or parenteral administration. The vehicles, fillers, diluents and excipient preferably used for solid preparation are: lactose, sucrose, starch, talc, cellulose, dextrin, kaolin and calcium carbonate. The liquid preparation for oral administration, i.e., emulsion, syrup and suspension include commonly used inactive diluent such as water and vegetable oil. The preparation may contain, other than the inactive diluent, auxiliaries such as moistening agents, suspending agents, sweetening agents, aromatic agents, coloring agents and preservatives. In addition, the preparation may be contained in, as the liquid preparation, a capsule made of an absorbed material such as gelatin. Examples of the solvents and suspending agents preferably used for preparing the preparation for the parenteral administration, i.e., injection and suppository are: water, propylene glycol, polyethylene glycol, benzyl alcohol, ethyl oleate and lecithin. Exemplified bases for the suppository include cacao butter, emulsificated cacao butter, laurin tallow and witepsol. The preparation can be made according to any one of ordinary methods.

The dosage relating to the present compound for oral administration to adults is generally in the range of between 0.01 to 1,000 mg as the daily dose. It is, however, preferable to control the dosage depending on the age, the degree of diseases and the symptom. The daily dose of the drug according to the present invention may be administered once a day. The same dose may also be administered two or three times a day at suitable intervals or on alternate days or so.

The daily dose of 0.001 to 100 mg relating to the present compound for injection to adults is preferably administered continuously or intermittently.

The aminoketone derivatives according to the present invention strongly inhibits thiol protease such as calpain, papain, cathepsin B, cathepsin H and cathepsin L or the like and has excellent properties concerning absorbance on oral administration, tissue distribution and cell membrane permeability. The aminoketone derivatives can thus be used as therapeutic agents for treating muscular dystrophy, cataract, cardiac infarction, stroke, Alzheimer's disease, amyotrophy, osteoporosis and hypercalcemia. It may also be used as a therapeutic agent for preventing metastasis of cancer. In addition, the present derivatives are also applicable as the intermediates upon preparation of ketone derivatives, which has the inhibitory activity against thiol protease, as disclosed in Japanese Patent Application No. 165094/1992.

The foregoing features of the present invention will be more readily apparent in the context of a specifically delineated set of examples and a reference. However, it should be understood that the present invention is not limited to those particular examples and the reference as long as not being depart from the spirit and scope of the appended claims.

EXAMPLE 1

Preparation of (S)-3-tert-butoxycarbonylamino-1-furfurylthio-2-heptanone (Compound No. 58 in Table 1)

6.54 g of (S)-3-tert-butoxycarbonylamino-1-chloro-2-heptanone and 3.11 g of furfuryl mercaptan were dissolved in 200 ml of tetrahydrofuran, to which 13 ml solution of 2N sodium hydroxide was added. The reaction solution was stirred at a room temperature for 17 hours and a sodium hydrogencarbonate solution was then added thereto. The solution was extracted with ethyl acetate. The extracted solution was washed with a saturated sodium chloride solution and dried over magnesium sulfate, which was then filtered, concentrated and purified by the silica gel column chromatography (eluent: 10% ethyl acetate containing hexane). The object of 7.82 g was obtained.

Yield: 92% IR(neat, cm$^{-1}$): 3353, 1705 NMR(CDCl$_3$, $\delta$): 0.89(t, J=6.6 Hz, 3H), 1.20–1.95(m, 6H), 1.44(s, 9H), 3.28(d, J=15 Hz, 1H), 3.39(d, J=15 Hz, 1H), 3.74(s, 2H), 4.52(m, 1H), 5.09(m, 1H), 6.22(d, J=2.9 Hz, 1H), 6.31(m, 1H), 7.36(m, 1H)

EXAMPLE 2

Preparation of (S)-3-amino-1-furfurylthio-2-heptanone hydrochloride (Compound No. 61 in Table 1)

7.8 g of (S)-3-tert-butoxycarbonylamino-1-furfurylthio-2-heptanone obtained in Example 1 was dissolved in 80 ml of ethyl acetate, to which 80 ml solution of 4N hydrogen chloride containing ethyl acetate was added. The reaction solution was stirred at a room temperature for 1 hour. Subsequently, 100 ml of hexane was added to the latter. Crystals generated were filtered and washed with hexane. The object of 5.93 g was obtained.

Yield: 93% IR(KBr, cm$^{-1}$): 3350, 1730, 1590 NMR(DMSO-d$_6$, $\delta$): 0.87(t, J=6.8 Hz, 3H), 1.16–1.40(m, 4H), 1.63–1.95(m, 2H), 3.55(d, J=16 Hz, 1H), 3.70(d, J=16 Hz, 1H), 3.81(s, 2H), 4.27(m, 1H), 6.30(m, 1H), 6.41(m, 1H), 7.61(m, 1H), 8.29(m, 3H)

EXAMPLE 3

Preparation of (S)-1-furfurylthio-3-phenoxyacetylamino-2-heptanone (Compound No. 66 in Table 1)

112 mg of (S)-3-amino-1-furfurylthio-2-heptanone hydrochloride obtained in Example 2 and 82 mg of phenoxyacetyl chloride were dissolved in 2 ml of methylene chloride. 89 mg of triethylamine was added to the reaction solution, which was then stirred at a room temperature for 3 hours. A solution of 1N hydrochloric acid was added thereto, which was extracted with methylene chloride. The extracted solution was successively washed with water, a saturated sodium hydrogencarbonate solution and a saturated sodium chloride solution. It was dried over sodium sulfate and filtered. The filtrate was concentrated and purified by the silica gel column chromatography (eluent: 20% ethyl acetate containing hexane). The object of 149 mg was obtained.

Yield: 98% IR(KBr, cm$^{-1}$) 3450, 1715, 1670 NMR(CDCl$_3$, $\delta$): 0.86(t, J=7.2 Hz, 3H), 1.05–1.40(m, 2H), 1.43–1.75(m, 1H), 1.80–2.07(m, 1H), 3.27(d, J=15 Hz, 1H), 3.34(d, J=15 Hz, 1H), 3.72(s, 2H), 4.52(s, 2H), 4.90(m, 1H), 6.21(d, J=2.5 Hz, 1H), 6.28(m, 1H), 6.90–7.58(m, 7H)

Similar operations were repeated to those made in Examples 1 through 3 to prepare the following compound values of physical properties thereof are shown below.

EXAMPLE 4 preparation of 1-tert-butoxycarbonylamino-3-furfurylthioacetone (Compound No. 1 in Table 1)

NMR(CDCl$_3$, $\delta$): 1.45(s, 9H), 3.23(s, 2H), 3.73(s, 2H), 4.14(d, J=4.5 Hz, 2H), 5.14(m, 1H), 6.23(m, 1H), 6.29(m, 1H), 7.39(m, 1H)

EXAMPLE 5

Preparation of 3-tert-butoxycarbonylamino-1-furfurylthio-3-methyl-2-butanone (Compound No. 28 in Table 1)

NMR(CDCl$_3$, $\delta$): 1.37–1.57(m, 15H), 3.49(s, 2H), 3.81(s, 2H), 5.05(br.s, 1H), 6.23(d, J=2.9 Hz, 1H), 6.29(m, 1H), 7.35(m, 1H)

EXAMPLE 6

Preparation of 3-amino-1-furfurylthio-3-methyl-2-butanone hydrochloride (Compound No. 30 in Table 1)

IR(KBr, cm$^{-1}$): 3356, 1730, 1610 NMR(CD$_3$OD, $\delta$): 1.59(s, 6H), 3.59(s, 2H), 3 83(s, 2H), 6.27(d, J=2.9 Hz, 1H), 6.34(m, 1H), 7.44(m, 1H)

EXAMPLE 7

Preparation of (S)-3-tert-butoxycarbonylamino-1-furfurylthio-4-methyl-2-pentanone (Compound No. 40 in Table 1)

NMR(CDCl$_3$, $\delta$): 0.81(d, J=6.8 Hz, 3H), 1.00(d, J=6.8 Hz, 3H), 1.44(s, 9H), 2.21(m, 1H), 3.28(d, J=15 Hz, 1H), 3.35(d, J=15 Hz, 1H), 3.75(s, 2H), 4.48(m, 1H), 5.06(d, J=8.5 Hz, 1H), 6.22(d, J=2.9 Hz, 1H), 6.30(m, 1H), 7.37(m, 1H)

EXAMPLE 8

Preparation of (S)-3-amino-1-furfurylthio-4-methyl-2-pentanone hydrochloride (Compound No. 42 in Table 1)

IR(KBr, cm$^{-1}$): 2966, 1730, 1589 NMR(CD$_3$OD, $\delta$): 0.96(d, J=7.0 Hz, 3H), 1.18(d, J=7.0 Hz, 3H), 2.51(m, 1H), 3.39(d, J=15 Hz, 1H), 3.62(d, J=15 Hz, 1H), 3.83(s, 2H), 4.38(m, 1H), 6.32(m, 1H), 6.40(m, 1H), 7.49(m, 1H)

EXAMPLE 9

Preparation of (S)-3-tert-butoxycarbonylamino-1-furfurylthio-2-hexanone (Compound No. 46 in Table 1)

NMR(CDCl$_3$, δ): 0.89(t, J=7.1 Hz, 3H), 1.18–1.59(m, 3H), 1.41(s, 9H), 1.76(m, 1H), 3.25(d, J=15 Hz, 1H), 3.30(d, J=15 Hz, 1H), 3.70(s, 2H), 4.45(m, 1H), 5.03(d, J=7.6 Hz, 1H), 6.19(d, J=2.6 Hz, 1H), 6.26(m, 1H), 7.32(m, 1H)

EXAMPLE 10

Preparation of (S)-3-amino-1-furfurylthio-2-hexanone hydrochloride (Compound No. 48 in Table 1)

IR(KBr, cm$^{-1}$): 2959, 1730, 1587 NMR(CDCl$_3$, δ): 0.98(t, J=7.2 Hz, 3H), 1.42–1.77(m, 2H), 1.82–2.13(m, 2H), 3.37(d, J=14 Hz, 1H), 3.43(d, J=14 Hz, 1H), 3.77(s, 2H), 4.59(dd, J=6.2 Hz, 5.2 Hz, 1H), 6.25–6.38(m, 2H), 7.36(m, 1H), 8.69(s, 3H)

EXAMPLE 11

Preparation of (S)-3-[3-(2-acetylamino-4-thiazolyl)-2-propenoylamino]-1-furfurylthio-2-heptanone (Compound No. 71 in Table 1)

IR(neat, cm$^{-1}$): 3280, 1720, 1695, 1660, 1625 NMR(CDCl$_3$, δ): 0.83(t, J=6.8 Hz, 3H), 1.17–1.42(m, 4H), 1.59(m, 1H), 1.89(m, 1H), 2.22(s, 3H), 3.35(d, J=15 Hz, 1H), 3.43(d, J=15 Hz, 1H), 3.74(s, 2H), 4.94(m, 1H), 6.20(d, J=3.2 Hz, 1H), 6.28(m, 1H), 6.66(d, J=15 Hz, 1H), 6.76(d, J=7.8 Hz, 1H), 7.02(s, 1H), 7.34(m, 1H), 7.49(d, J=15 Hz, 1H), 10.3(s, 1H)

EXAMPLE 12

Preparation of (S)-1-furfurylthio-3-[(2-phenylamino-4-thiazolyl)acetylamino]-2-heptanone (Compound No. 75 in Table 1)

IR(neat, cm$^{-1}$): 3300, 1720, 1705, 1660, 1600 NMR(CDCl$_3$, δ): 0.82(t, J=6.9 Hz, 3H), 1.12–1.38(m, 4H), 1.58(m, 1H), 1.85(m, 1H), 3.24(d, J=15 Hz, 1H), 3.34(d, J=15 Hz, 1H), 3.59(s, 2H), 3.69(s, 2H), 4.75(m, 1H), 6.19(d, J=2.8 Hz, 1H), 6.27(m, 1H), 6.39(s, 1H), 7.06(m, 1H), 7.21–7.41(m, 6H), 7.52(d, J=7.7 Hz, 1H)

EXAMPLE 13

Preparation of (S)-3-tert-butoxycarbonylamino-1-(3-furylmethylthio)-2-heptanone (Compound No. 76 in Table 1)

NMR(CDCl$_3$, δ): 0.90(d, J=6.2 Hz, 3BE), 1.13–1.60(m, 5H), 1.47(s, 9H), 1.81(m, 1H), 3.20(d, J=15 Hz, 1H), 3.29(d, J=15 Hz, 1H), 3.55(s, 2H), 4.49(m, 1H), 5.05(d, J=5.8 Hz, 1H), 6.39(d, J=1.2 Hz, 1H), 7.35–7.42(m, 2H)

EXAMPLE 14

Preparation of (S)-3-benzyloxycarbonylamino-1-furfurylthio-5-methyl-2-hexanone (Compound No. 53 in Table 1)

IR(neat, cm$^{-1}$): 3350, 1720, 1700, 1620 NMR(CDCl$_3$,δ): 0.88–1.02(m, 6H), 1.42(m, 1H), 1.55–1.80(m, 2H), 3.29(d, J=8.5 Hz, 1H), 3.35(d, J=8.5 Hz, 1H), 3.73(s, 2H), 4.61(m, 1H), 5.11(s, 2H), 5.20(d, J=8.2 Hz, 1H), 6.21(m, 1H), 6.28(m, 1H), 7.26–7.40(m, 6H)

EXAMPLE 15

Preparation of (S)-3-tert-butoxycarbonylamino-1-(3-thienylmethylthio)-2-heptanone (Compound No. 82 in Table 1)

Melting Point: 43°–45° C. IR(KBr, cm$^{-1}$): 3383, 1705, 1686, 1510 NMR(CDCl$_3$, δ): 0.89(t, J=6.7 Hz, 3H), 1.18–1.40(m, 4H), 1.45(s, 9H), 1.52(m, 1H), 1.80(m, 1H), 3.17(d, J=14.8 Hz, 1H), 3.27(d, J=14.8 Hz, 1H), 3.73(s, 2H), 4.49(m, 1H), 5.05(br.d, J=7.6 Hz, 1H), 7.06(d, J=5.0 Hz, 1H), 7.16(br.s, 1H), 7.29(m, 1H)

EXAMPLE 16

Preparation of (S)-3-amino-1-(3-thienylmethylthio)-2-heptanone hydrochloride (Compound No. 84 in Table 1)

Melting Point: 91°–94° C. IR(KBr, cm$^{-1}$): 1730, 1588, 1505 NMR(CD$_3$OD, δ): 0.95(t, J=6.8 Hz, 3H), 1.20–1.44(m, 4H), 1.78(m, 1H), 1.96(m, 1H), 3.30(d, J=].4.9 Hz, 1H), 3.49(d, J=14.9 Hz, 1H), 3.79(s, 2H), 4.34(dd, J=7.8 Hz, 4.3 Hz, 1H), 7.09(dd, J=5.0 Hz, 1.3 Hz, 1H), 7.26(dd, J=2.1 Hz, 1.3 Hz, 1H), 7.39(dd, J=5.0 Hz, 3.0 Hz, 1H)

EXAMPLE 17

Preparation of (S)-3-phenoxyacetylamino-1-(3-thienylmethylthio)-2-heptanone (Compound No. 86 in Table 1)

IR(neat, cm$^{-1}$): 3406, 1678, 1522 NMR(CDCl$_3$, δ): 0.87(t, J=6.7 Hz, 3H), 1.10–1.40(m, 4H), 1.52(m, 1H), 1.90(m, 1H), 3.16(d, J=14.6 Hz, 1H), 3.25(d, J=14.6 Hz, 1H), 3.72(s, 2H), 4.53(s, 2H), 4.93(m, 1H), 6.96(d, J=8.5 Hz, 2H), 7.01(m, 1H), 7.05(d, J=6.5 Hz, 1H), 7.16(br.s, 1H), 7.30(m, 1H), 7.37(m, 2H)

EXAMPLE 18

Preparation of (S)-3-(3-methoxyphenoxyacetylamino)-1-(3-thienylmethylthio)-2-heptanone (Compound No. 87 in Table 1)

IR(neat, cm$^{-1}$): 3407, 1678, 1603, 1522 NMR(CDCl$_3$, δ): 0.86(t, J=6.8 Hz, 3H), 1.10–1.40(m, 4H), 1.60(m, 1H), 1.90(m, 1H), 3.16(d, J=14.7 Hz, 1H), 3.25(d, J=14.7 Hz, 1H), 3.72(s, 2H), 3.81(s, 3H), 4.51(d, J=1.2 Hz, 2H), 4.92(m, 1H), 6.52(d, J=1.4 Hz, 1H), 6.53–6.61(m, 2H), 7.05(dd, J=5.0 Hz, 1.3 Hz, 1H), 7.11(br.d, J=7.9 Hz, 1H), 7.15(d, J=1.1 Hz, 1H), 7.22(ddd, J=8.4 Hz, 8.4 Hz, 1.0 Hz, 1H), 7.28(dd, 5.0 Hz, 3.0 Hz, 1H)

EXAMPLE 19

Preparation of (S)-3-acetoxyacetylamino-1-(3-thienylmethylthio)-2-heptanone (Compound No. 89 in Table 1)

IR(neat, c$^{-1}$): 3310, 1.752, 1674, 1530 NMR(CDCl$_3$, δ): 0.89(t, J=6.7 Hz, 3H), 1.15–1.40(m, 4H), 1.60(m, 1H), 1.90(m, 1H), 2.21(s, 3H), 3.17(d, J=14.7 Hz, 1H), 3.26(d, J=14.7 Hz, 1H), 3.73(s, 2H), 4.59(s, 2H), 4.91(m, 1H), 6.72(br.d, J=6.7 Hz, 1H), 7.06(d, J=4.9 Hz, 1H), 7.16(br.s, 1H), 7.29(dd, J=4.9 Hz, 3.1 Hz, 1H)

EXAMPLE 20

Preparation of (S)-3-(3-phenoxybenzoylamino)-1-(3-thienylmethylthio)-2-heptanone (Compound No. 93 in Table 1)

IR(neat, cm$^{-1}$): 3320, 1711, 1645, 1579, 1531 NMR(CDCl$_3$, δ): 0.88(t, J=6.8 Hz, 3H), 1.15–1.40(m, 4H), 1.64(m, 1H), 2.00(m, 1H), 3.22(d, J=14.7 Hz, 1H), 3.31(d, J=14.7 Hz, 1H), 3.74(s, 2H), 5.03(m, 1H), 6.71(br.d, J=7 Hz, 1H), 7.02–7.06(m, 3H), 7.13–7.16(m, 3H), 7.30–7.42(m, 4H), 7.47–7.51(m, 3H)

EXAMPLE 21

Preparation of (S)-3-tert-butoxycarbonylamino-4-cyclohexyl-1-furfurylthio-2-butanone (Compound No. 109 in Table 1)

NMR(CDCl$_3$, δ): 0.80–1.08(m, 2H), 1.12–1.53(m, 6H), 1.45(s, 9H), 1.55–1.78(m, 4H), 1.80–1.95(m, 1H), 3.30(d, J=11 Hz, 1H), 3.38(d, J=11 Hz, 1H), 3.74(s, 2H), 4.54(m, 1H), 5.92(d, J=7.1 Hz, 1H), 6.23(m, 1H), 6.30(m, 1H), 7.36(m, 1H)

EXAMPLE 22

Preparation of (S)-4-tert-butoxycarbonylamino-6-furfurylthio-5-oxohexanoic acid methyl ester (Compound No. 115 in Table 1)

NMR(CDCl$_3$, δ): 1.40(s, 9H), 1.63–1.85(m, 2H), 2.05–2.42(m, 2H), 3.27(d, J=15 Hz, 1H), 3.35(d, J=15 Hz, 1H), 3.64(s, 3H), 3.69(s, 2H), 4.52(m, 1H), 5.19(d, J=5.7 Hz, 1H), 6.19(d, J=3.2 Hz, 1H), 6.27(m, 1H), 7.35(m, 1H)

EXAMPLE 23

Preparation of 1-tert-butoxycarbonylamino-1-(3-pyridylmethylthioacetyl) cyclohexane (Compound No. 130 in Table 1)

NMR(CDCl$_3$, δ): 1.31–1.58(m, 10H), 1.58–1.73(m, 7H), 1.83–2.11(m, 2H), 3.41(s, 2H), 3.79(s, 2H), 5.52(s, 1H), 7.24(m, 1H), 7.73(ddd, J=8.1 Hz, 1.8 Hz, 1.8 Hz, 1H), 8.48(m, 1H), 8.57(s, 1H)

EXAMPLE 24

Preparation of 1-amino-1-(3-pyridylmethylthioacetyl) cyclohexane hydrochloride (Compound No. 132 in Table 1)

NMR(CD$_3$OD, δ): 1.37–1.72(m, 4H), 1.72–1.92(m, 4H), 2.04–2.22(m, 2H), 3.75(s, 2H), 4.08(s, 2H), 8.11(dd, J=8.1 Hz, 5.9 Hz, 1H), 8.73(d, J=8.1 Hz, 1H), 8.81(d, J=5.9 Hz, 1H), 8.96(s, 1H)

EXAMPLE 25

Preparation of (S)-3-tert-butoxycarbonylamino-1-furfurylthio-4-phenyl-2-butanone (Compound No. 151 in Table 1)

NMR(CDCl$_3$, δ): 1.41(s, 9H), 2.90–3.15(m, 2H), 3.17(d, J=14 Hz, 1H), 3.26(d, J=14 Hz, 1H), 3.65(s, 2H), 4.73(dt, J=6.8 Hz, 6.6 Hz, 1H), 5.06(d, J=6.8 Hz, 1H), 6.18(d, J=3.2 Hz, 1H), 6.29(dd, J=3.2 Hz, 1.9 Hz, 1H), 7.10–7.22(m, 2H), 7.22–7.38(m, 4H)

EXAMPLE 26

Preparation of (S)-3-amino-1-furfurylthio-4-phenyl-2-butanone hydrochloride (Compound No. 161 in Table 1)

NMR (DMSO-d$_6$, δ): 3.02–3.23(m, 2H), 3.36(d, J=16 Hz, 1H), 3.59(d, J=16 Hz, 1H), 3.69(d, J=14 Hz, 1H), 3.87(d, J=14 Hz, 1H), 4.54(m, 1H), 6.24(d, J=3.1 Hz, 1H), 6.38(dd, J=3.1 Hz, 1.9 Hz, 1H), 7.20–7.40(m, 5H), 7.57(d, J=1.9 Hz, 1H), 8.47(s, 3H)

EXAMPLE 27

Preparation of (S)-3-(N-tert-butoxycarbonyl-N-methylamino)-1-furfurylthio-4-phenyl-2-butanone (Compound No. 152 in Table 1)

NMR(CDCl$_3$, δ): 1.35(s, 5.4H), 1.40(s, 3.6H), 2.57(s, 1.2H), 2.62(s, 1.8H), 2.80–3.05(m, 1H), 3.12–3.43(m, 3H), 3.66(s, 0.8H), 3.67(s, 1.2H), 4.60–4.82(m, 1H), 6.20(d, J=2.8 Hz, 1H), 6.31(m, 1H), 7.10–7.43(m, 6H)

EXAMPLE 28 preparation of (S)-1-furfurylthio-3-isobutoxycarbonylamino-4-phenyl-2-butanone (Compound No. 153 in Table 1)

Melting Point: 58°–59° C. IR(KBr, cm$^{-1}$): 3330, 1725, 1683 NMR(CDCl$_3$, δ): 0.90(d, J=6.7 Hz, 6H), 1.88(m, 1H), 2.95–3.15(m, 2H), 3.18(s, 2H), 3.64(s, 2H), 3.83(d, J=6.7 Hz, 2H), 4.78(m, 1H), 5.21(d, J=7.2 Hz, 1H), 6.18(d, J=3.3 Hz, 1H), 6.29(dd, J=3.3 Hz, 1.9 Hz, 1H), 7.10–7.18(m, 2H), 7.18–7.38(m, 4H)

EXAMPLE 29

Preparation of (S)-3-benzyloxycarbonylamino-1-furfurylthio-4-phenyl-2-butanone (Compound No. 155 in Table 1)

Melting Point: 64°–6620 C. IR(KBr, cm$^{-1}$): 3320, 1730, 1640 NMR(CDCl$_3$, δ): 2.95–3.25(m, 2H), 3.17(s, 2H), 3.63(s, 2H), 4.84(d, J=7.5 Hz, 1H), 5.08(s, 2H), 5.33(d, J=7.5 Hz 1H), 6.17(m, 1H), 6.27(m, 1H), 7.10–7.45(m, 11H)

EXAMPLE 30

Preparation of (S)-3-fluorenylmethoxycarbonylamino-1-furfurylthio-4-phenyl-2-butanone (Compound No. 159 in Table 1)

NMR(CDCl$_3$, δ): 2.95–3.10(m, 2H), 3.15<s, 2H), 3.64(s, 2H), 4.19(t, J=6.7 Hz, 1H), 4.30–4.50(m, 2H), 4.84(q, J=7.5 Hz, 1H), 5.31(d, J=7.5 Hz, 1H), 6.17(m, 1H), 6.27(m, 1H), 7.10–7.16(m, 2H), 7.20–7.45(m, 8H), 7.50–7.60(m, 2H), 7.75–7.79(m, 2H)

EXAMPLE 31

Preparation of (S)-3-(2,5-dioxo-1-pyrrolidyloxycarbonylamino)-1-furfurylthio-4-phenyl-2-butanone (Compound No. 160 in Table 1)

NMR(CDCl$_3$, δ): 3.04(m, 2H), 3.17(s, 2H), 3.65(s, 4H), 3.68(s, 2H), 4.83(q, J=7.3 Hz, 1H), 5.21(d, J=7.3 Hz, 1H), 6.18(m, 1H), 6.29(m, 1H), 7.14–7.35(m, 6H)

EXAMPLE 32

Preparation of (S)-1-furfurylthio-3-isovalerylamino-4-phenyl-2-butanone (Compound No. 163 in Table 1)

Melting Point: 94°–95° C. IR(KBr, cm$^{-1}$): 3320, 1712, 1643 NMR(CDCl$_3$, δ): 0.87(d, J=6.2 Hz, 3H), 0.89(d, J=5.6 Hz, 3H), 1.53(m, 1H), 2.03(m, 2H) 2.95–3.20(m, 2H), 3.19(s, 2H), 3.65(s, 2H), 5.07(dt, J=7.2 Hz, 6.5 Hz, 1H), 5.91(d, J=7.2 Hz, 1H), 6.18(d, J=3.1 Hz, 1H), 6.29(dd, J=3.1 Hz, 2.0 Hz, 1H), 7.05–7.38(m, 6H)

EXAMPLE 33

Preparation of (S)-1-furfurylthio-3-isohexanoylamino-4-phenyl-2-butanone (Compound No. 164 in Table 1)

Melting Point: 68°–71° C. IR(KBr, cm$^{-1}$): 3320, 1710, 1640 NMR(CDCl$_3$, δ): 0.87(d, J=4.5 Hz, 6H), 1.40–1.60(m, 3H), 2.17(t, J=7.8 Hz, 2H), 2.95–3.20(m, 2H), 3.20(s, 2H), 3.66(s, 2H), 5.05(q, J=7.2 Hz, 1H), 5.93(d, J=7.2 Hz, 1H), 6.19(m, 1H), 6.29(m, 1H), 7.12–7.40(m, 6H)

EXAMPLE 34

Preparation of (S)-1-furfurylthio-4-phenyl-3-(3-phenyl-propyonylamino)-2-butanone (Compound No. 166)

NMR(CDCl$_3$, δ): 2.48(m, 2H), 2.92(t, J=7.6 Hz, 2H), 3.01(m, 2H), 3.12(s, 2H), 3.61(s, 2H), 5.03(q, J=7.2 Hz, 1H), 5.89(d, J=7.2 Hz, 1H), 6.16(m, 1H), 6.28(m, 1H), 7.01–7.06(m, 2H), 7.15–7.35(m, 9H)

EXAMPLE 35

Preparation of (S)-1-furfurylthio-3-(1-naphtylacetylamino)-4-phenyl-2-butanone (Compound No. 168 in Table 1)

NMR(CDCl$_3$, δ): 2.75–2.95(m, 2H), 3.07(s, 2H), 3.51(s, 2H), 3.99(s, 2H), 4.90(q, J=7.5 Hz, 1H), 5.79(d, J=7.5 Hz, 1H), 6.11(m, 1H), 6.26(m, 1H), 6.65–6.72(m, 2H), 6.96–7.10(m, 3H), 7.20–7.35(m, 3H), 7.40–7.55(m, 2H), 7.80–7.92(m, 2H)

EXAMPLE 36

Preparation of (S)-1-furfurylthio-3-(2-naphtylacetylamino)-4-phenyl-2-butanone (Compound No. 169 in Table 1)

NMR(CDCl$_3$, δ): 2.87(dd, J=14 Hz, 7.1 Hz, 1H), 3.01(dd, J=14 Hz, 7.1 Hz, 1H), 3.18(s, 2H), 3.61(s, 2H), 3.69(s, 2H), 4.96(q, J=7.0 Hz, 1H), 5.88(d, J=7.0 Hz, 1H), 6.15(m, 1H), 6.27(m, 1H), 6.84–6.89(m, 2H), 7.0–7.12(m, 3H), 7.23(m, 1H), 7.32(m, 1H), 7.49–7.53(m, 2H), 7.62(s, 1H), 7.76–7.87(m, 3H)

EXAMPLE 37

Preparation of (S)-3-cyclohexyloxyacetylamino-1-furfurylthio-4-phenyl-2-butanone (Compound No. 170 in Table 1)

IR (neat, cm$^{-1}$): 3410, 1710, 1670 NMR(CDCl$_3$, δ): 1.16–1.40(m, 5H), 1.45–1.85(m, 5H), 3.10(m, 2H), 3.19(s, 2H), 3.21(m, 1H), 3.64(s, 2H), 3.92(s, 2H) 5.04(q, J=7.0 Hz, 1H), 6.19(m, 1H), 6.29(m, 1H), 7.12–7.36(m, 7H)

EXAMPLE 38

Preparation of (S)-1-furfurylthio-3-phenoxyacetylamino-4-phenyl-2-butanone (Compound No. 171 in Table 1)

IR(KBr, cm$^{-1}$): 3350, 1700, 1655 NMR(CDCl$_3$, δ): 3.0–3.16(m, 2H), 3.16(s, 2H), 3.63(s, 2H) 4.47(s, 2H), 5.14(q, J=7.2 Hz, 1H), 6.17(m, 1H), 6.28(m, 1H), 6.85–6.90(m, 2H), 7.03(t, J=7.0 Hz, 1H), 7.10–7.16(m, 2H), 7.20–7.38(m, 6H)

EXAMPLE 39

Preparation of (S)-3-(2-chlorophenoxyacetylamino)-1-furfurylthio-4-phenyl-2-butanone (Compound No. 172 in Table 1)

NMR(CDCl$_3$, δ): 3.11(m, 2H), 3.20(s, 2H), 3.66(s, 2H), 4.46(d, J=14 Hz, 1H), 4.54(d, J=14 Hz, 1H), 5.13(q, J=7.2 Hz, 1H), 6.19(m, 1H), 6.28(m, 1H), 6.84(d, J=8.1 Hz, 1H), 6.99(m, 1H), 7.16–7.42(m, 9H)

EXAMPLE 40 preparation of (S)-3-(4-chlorophenoxyacetylamino)-1-furfurylthio-4-phenyl-2-butanone (Compound No. 174 in Table 1)

Melting Point: 95°–98° C. IR(KBr, cm$^{-1}$): 3280, 1730, 1670 NMR(CDCl$_3$, δ): 3.08(m, 2H), 3.17(s, 2H), 3.63(s, 2H) 4.44(s, 2H), 5.14(q, J=7.0 Hz, 1H), 6.18(m, 1H), 6.29(m, 1H), 6.75–6.82(m, 2H), 7.02–7.36(m, 9H)

EXAMPLE 41

Preparation of (S)-1-furfurylthio-3-(3-methylphenoxyacetylamino)-4-phenyl-2-butanone (Compound No. 176 in Table 1)

Melting Point: 76°–78° C. IR(KBr, cm$^{-1}$): 3279, 1730, 1669, 1609 NMR(CDCl$_3$, δ): 2.34(s, 3H), 3.0–3.17(m, 2H), 3.15(s, 2H), 3.62(s, 2H), 4.46(s, 2H), 5.13(dt, J=7.6 Hz, 6.9 Hz, 1H), 6.18(d, J=3.1 Hz, 1H), 6.28(dd, J=3.1 Hz, 1.9 Hz, 1H), 6.60–6.73(m, 2H), 6.85(d, J=7.9 Hz, 1H), 7.05–7.37(m, 8H)

EXAMPLE 42

Preparation of (S)-1-furfurylthio-4-phenyl-3-(3-trifluoromethylphenoxyacetylamino)-2-butanone (Compound No. 179 in Table 1)

Melting Point: 72°–80° C. IR(KBr, cm$^{-1}$): 3414, 1711, 1684 NMR(CDCl$_3$, δ): 3.02–3.23(m, 2H), 3.17(s, 2H), 3.64(s, 2H), 4.47(d, J=15 Hz, 1H), 4.54(d, J=15 Hz, 1H), 5.15(dt, J=7.5 Hz, 6.8 Hz, 1H), 6.19(d, J=3.1 Hz, 1H), 6.29(dd, J=3.1 Hz, 1.9 Hz, 1H), 6.98–7.53(m, 11H)

EXAMPLE 43

Preparation of (S)-1-furfurylthio-3-(3-methoxyphenoxyacetylamino)-4-phenyl-2-butanone (Compound No. 182 in Table 1)

IR(KBr, cm$^{-1}$) 3281, 1730, 1671, 1603 NMR(CDCl$_3$, δ): 3.0–3.23(m, 2H), 3.15(s, 2H), 3.62(s, 2H), 3.80(s, 3H), 4.46(s, 2H), 5.13(dt, J=7.7 Hz, 6.8 Hz, 1H), 6.17(d, J=3.2 Hz, 1H), 6.28(dd, J=3.2 Hz, 2.0 Hz, 1H), 6.35–6.52(m, 2H), 6.50–6.63(m, 1H), 7.0–7.40(m, 8H)

EXAMPLE 44

Preparation of
(S)-1-furfurylthio-3-(2-methoxyphenoxyacetylamino)-4-phenyl-2-butanone (Compound No. 181 in Table 1)

NMR(CDCl$_3$, δ): 2.96–3.20(m, 2H), 3.15(s, 2H), 3.61(s, 2H), 3.84(s, 3H), 4.53(s, 2H), 5.12(q, J=7.5 Hz, 1H), 6.16(m, 1H), 6.27(m, 1H), 6.83–7.36(m, 10H), 7.65(d, J=7.5 Hz, 1H)

EXAMPLE 45

Preparation of
(S)-1-furfurylthio-3-(2-phenoxypropyonylamino)-4-phenyl-2-butanone (Compound No. 184 in Table 1)

NMR(CDCl$_3$, δ): 1.43(d, J=6.3 Hz, 1.5H), 1.54(d, J=6.23 Hz, 1.5H), 2.95–3.20(m, 4H), 3.50(s, 1H), 3.65(s, 1H), 4.64(m, 1H), 5.02(m, 1H), 6.12(m, 0.5H), 6.20(m, 0.5H), 6.25(m, 0.5H), 6.29(m, 0.5H), 6.79–7.04(m, 5H), 7.08–7.40(m, 7H)

EXAMPLE 46

Preparation of
(S)-1-furfurylthio-3-(2-phenoxybutyrylamino)-4-phenyl-2-butanone (Compound No. 185 in Table 1)

NMR(CDCl$_3$, δ): 0.89(t, J=7.3 Hz, 1.5H), 1.01(t, J=7.3 Hz, 1.5H), 1.50–2.0(m, 2H), 2.99(s, 1H), 3.19(s, 1H), 2.92–3.20(m, 2H), 3.48(s, 1H), 3.64(s, 1H), 4.47(m, 1H), 5.04(q, J=7.3 Hz, 1H), 6.10(m, 0.5H), 6.19(m, 0.5H), 6.26(m, 0.5H), 6.30(m, 0.5H), 6.78–7.04(m, 5H), 7.10–7.36(m, 7H)

EXAMPLE 47

Preparation of
(S)-3-benzyloxyacetylamino-1-furfurylthio-4-phenyl-2-butanone (Compound No. 186 in Table 1)

NMR(CDCl$_3$, δ): 2.95–3.20(m, 2H), 3.18(s, 2H), 3.64(s, 2H), 3.90(d, J=15 Hz, 1H), 3.99(d, J=15 Hz, 1H), 4.46(d, J=14 Hz, 1H), 4.55(d, J=14 Hz, 1H), 5.06(q, J=7.3 Hz, 1H), 6.18(d, J=2.9 Hz, 1H), 6.28(m, 1H), 7.0–7.45(m, 12H)

EXAMPLE 48

Preparation of
(S)-1-furfurylthio-3-(1-naphtoxyacetylamino)-4-phenyl-2-butanone (Compound No. 188 in Table 1)

Melting Point: 104°–106° C. IR(KBr, cm$^{-1}$): 3310, 1710, 1665 NMR(CDCl$_3$, δ): 3.12(m, 2H), 3.22(s, 2H), 3.65(s, 2H), 4.62(d, J=13 Hz, 1H), 4.71(d, J=13 Hz, 1H), 5.18(q, J=7.5 Hz, 1H), 6.18(m, 1H), 6.28(m, 1H), 6.74(d, J=7.3 Hz, 1H), 7.05–7.36(m, 8H), 7.48–7.60(m, 3H), 7.84(m, 1H), 8.05(m, 1H)

EXAMPLE 49

Preparation of
(S)-1-furfurylthio-3-(2-naphtoxyacetylamino)-4-phenyl-2-butanone (Compound No. 189 in Table 1)

Melting Point: 115°–118° C. IR(KBr, cm$^{-1}$): 3300, 1730, 1670 NMR(CDCl$_3$, δ): 3.05–3.18(m, 2H), 3.16(s, 2H), 3.60(s, 2H), 4.60(s, 2H), 5.15(q, J=7.5 Hz, 1H), 6.16(m, 1H), 6.27(m, 1H), 7.05–7.20(m, 10H), 7.35–7.50(m, 2H), 7.70–7.82(m, 1H)

EXAMPLE 50

Preparation of
(S)-1-furfurylthio-4-phenyl-3-phenylthioacetylamino-2-butanone (Compound No. 190 in Table 1)

IR(KBr, cm$^{-1}$): 3460, 3300, 1730, 1670 NMR(CDCl$_3$, δ): 2.99(m, 2H), 3.05(s, 2H), 3.57(s, 2H), 3.60(s, 2H), 4.99(q, J=7.0 Hz, 1H), 6.15(m, 1H), 6.28(m, 1H), 7.03–7.09(m, 2H), 7.16–7.35(m, 10H)

EXAMPLE 51 preparation of
(S)-3-(2-benzofuranylcarbonylamino)-1-furfurylthio-4-phenyl-2-butanone (Compound No. 198 in Table 1)

NMR(CDCl$_3$, δ): 3.20(s, 2H), 3.21(d, J=5.7 Hz, 2H), 3.66(s, 2H), 5.31(q, J=7.7 Hz, 1H), 6.19(m, 1H), 6.25(m, 1H), 7.18–7.35(m, 8H), 7.40–7.53(m, 3H), 7.68(d, J=7.7 Hz, 1H)

EXAMPLE 52

Preparation of
(S)-3-(2-chromanylcarbonylamino)-1-furfurylthio-4-phenyl-2-butanone (Compound No. 202 in Table 1)

IR(KBr, cm$^{-1}$): 3300, 1710, 1650 NMR(CDCl$_3$, δ): 1.85–2.08(m, 1H), 2.20–2.45(m, 1H), 2.52–2.88(m, 2H), 2.95(dd, J=14 Hz, 7.5 Hz, 0.5H), 3.05–3.31(m, 3.5H), 3.58(s, 1H), 3.67(s, 1H), 4.51(m, 1H), 5.02(q, J=7.5 Hz, 0.5H), 5.11(m, 0.5H), 6.25(d, J=2.0 Hz, 0.5H), 6.26(d, J=1.9 Hz, 0.5H), 6.29(m, 0.5H), 6.30(m, 0.5H), 6.80–6.95(m, 2H), 6.99–7.39(m, 9H)

EXAMPLE 53

Preparation of
(S)-3-tert-butoxycarbonylamino-1-(3-furylmethylthio)-4-phenyl-2-butanone (Compound No. 204 in Table 1)

IR(KBr, cm$^{-1}$): 3370, 1705, 1680 NMR(CDCl$_3$, 67): 1.41(s, 9H), 2.88–3.22(m, 4H), 3.45(s, 2H), 4.76(dt, J=7.2 Hz, 6.8 Hz, 1H), 5.04(d, J=7.2 Hz, 1H), 6.36(d, J=0.7 Hz, 1H), 7.10–7.42(m, 7H)

EXAMPLE 54

Preparation of
(S)-1-furfurylthio-3-(4-oxo-4H-1-benzopyran-2-ylcarbonylamino)-4-phenyl-2-butanone (Compound No. 203 in Table 1)

IR(KBr, cm$^{-1}$): 3520, 1720, 1650 NMR(CDCl$_3$, δ): 3.20(s, 2H), 3.21(d, J=7.9 Hz, 2H), 3.67(s, 2H), 5.30(q, J=7.2 Hz, 1H), 6.19(m, 1H), 6.28(m, 1H), 7.19–7.37(m, 6H), 7.43–7.53(m, 3H), 7.75(m, 1H), 8.22(dd, J=17 Hz, 8 HZ, 1H)

EXAMPLE 55

Preparation of
(S)-3-tert-butoxycarbonylamino-4-phenyl-1-(3-thienylmethylthio)-2-butanone (Compound No. 210 in Table 1)

IR(KBr, cm$^{-1}$): 3378, 1711, 1682 NMR(CDCl$_3$, δ): 1.41(s, 9H), 2.85–3.20 (m, 4H), 3.63(s, 2H), 4.74(m, 1H), 5.05(d, J=7.6 Hz, 1H), 7.01(dd, J=4.9 Hz, 1.1 Hz, 1H), 7.05–7.55(m, 7H)

EXAMPLE 56

Preparation of (S)-3-amino-4-phenyl-1-(3-thienylmethylthio)-2-butanone hydrochloride (Compound No. 213 in Table 1)

IR(KBr, cm$^{-1}$): 3072, 1723, 1599 NMR(CD$_3$OD, δ): 3.01(dd, J=14 Hz, 8.4 Hz, 1H), 3.13–3.42(m, 3H), 3.75(s, 2H), 4.63(t, J=6.2 Hz, 1H), 7.07(dd, J=5.0 Hz, 1.3 Hz, 1H), 7.18–7.47(m, 7H)

EXAMPLE 57

Preparation of (S)-3-phenoxyacetylamino-4-phenyl-1-(3-thienylmethylthio)-2-butanone (Compound No. 214 in Table 1)

Melting Point: 80°–81° C. IR(KBr, cm$^{-1}$): 3281, 1732, 1669, 16011 NMR(CDCl$_3$, δ): 2.95–3.20(m, 4H), 3.61(s, 2H), 4.44(d, J=15 Hz, 1H), 4.51(d, J=15 Hz, 1H), 5.15(dt, J=7.7 Hz, 6.9 Hz, 1H), 6.88(d, J=8.2 Hz, 2H), 6.95–7.40(m, 12H)

EXAMPLE 58

Preparation of (S)-3-(3-methoxyphenoxyacetylamino)-4-phenyl-1-(3-thienylmethylthio)-2-butanone (Compound No. 216 in Table 1)

IR(neat, cm$^{-1}$): 3407, 1715, 1678, 1603 NMR(CDCl$_3$, δ): 2.97–3.15(m, 4H), 3.61(s, 2H), 3.80(s, 3H), 4.46(s, 2H), 5.14(dt, J=7.8 Hz, 6.8 Hz, 1H), 6.40–6.50(m, 2H), 6.53–6.63(m, 1H), 7.01(dd, J=5.0 Hz, 1.3 Hz, 1H), 7.05–7.35(m, 9H)

EXAMPLE 59

Preparation of (S)-3-(4-methoxyphenoxyacetylamino)-4-phenyl-1-(3-thienylmethylthio)-2-butanone (Compound No. 217 in Table 1)

Melting Point: 80°–81° C. IR(KBr, cm$^{31}$ $^1$): 3281, 1726, 1663 NMR(CDCl$_3$, δ): 2.95–3.17(m, 4H), 3.62(s, 2H), 3.78(s, 3H), 4.39(d, J=15 Hz, 1H), 4.45(d, J=15 Hz, 1H), 5.14(dt, J=7.7 Hz, 7.0 Hz, 1H), 6.73–6.88(m, 4H), 7.01(dd, J=4.9 Hz, 1.0 Hz, 1H), 7.05–7.38(m, 8H)

EXAMPLE 60

Preparation of (S)-3-(2,4-dimethoxycinnamoylamino)-4-phenyl-1-(3-thienylmethylthio)-2-butanone (Compound No. 219 in Table 1)

Melting Point: 142°–143° C. IR(KBr, cm$^{-1}$): 3331, 1719, 1647, 1607 NMR(CDCl$_3$, δ): 3.04–3.22(m, 4H), 3.65(s, 2H), 3.84(s, 3H), 3.87(s, 3H), 5.19(dd, J=7.0 Hz, 6.4 Hz, 1H), 6.08(d, J=7.0 Hz, 1H), 6.35–6.55(m, 3H), 7.02(d, J=4.9 Hz, 1H), 7.07–7.38(m, 7H), 7.39(d, J=8.4 Hz, 1H), 7.89(d, J=16 Hz, 1H)

EXAMPLE 61

Preparation of (S)-3-tert-butoxycarbonylamino-4-phenyl-1-(2-pyridylmethylthio)-2-butanone (Compound No. 226 in Table 1)

NMR(CDCl$_3$, δ): 1.40(s, 9H), 2.90–3.15(m, 2H), 3.19(d, J=10 Hz, 1H), 3.30(d, J=10 Hz, 1H), 3.75(s, 2H), 4.72(dt, J=7.2 Hz, 6.5 Hz, 1H), 5.13(d, J=7.2 Hz, 1H), 7.08–7.35(m, 7H), 7.63(td, J=7.6 Hz, 1.9 Hz, 1H), 8.54(m, 1H)

EXAMPLE 62

Preparation of (S)-3-tert-butoxycarbonylamino-1-(2-oxazolidinone-4-ylmethylthio)-4-phenyl-2-butanone (Compound No. 223 in Table 1)

NMR(CDCl$_3$, δ): 1.41(s, 9H), 2.45–2.70(m, 2H), 2.93–3.05(m, 2H) 3.05–3.42(m, 2H), 3.90(m, 1H), 4.06(m, 1H), 4.45(m, H), 4.73(m, 1H), 5.11(m, 1H), 5.85–6.10(m, 1H), 7.17(d, J=7.9 Hz, 2H), 7.24–7.38(m, 3H)

EXAMPLE 63

Preparation of (S)-3)-tert-butoxycarbonylamino-4-(4-fluorophenyl)-1-furfurylthio-2-butanone (Compound No. 241 in Table 1)

NMR(CDCl$_3$, δ): 1.41(s, 9H), 2.87–3.14(m, 2H), 3.17(d, J=15 Hz, 1H), 3.25(d, J=15 Hz, 1H), 3.65(s, 2H), 4.69(m, 1H), 5.02(d, J=6.2 Hz, 1H), 6.19(d, J=3.3 Hz, 1H), 6.29(m, 1H), 6.98(dd, J=7.5 Hz, 6.4 Hz, 2H), 7.09(dd, J=23 Hz, 6.4 Hz, 2H), 7.35(m, 1H)

EXAMPLE 64

Preparation of (S)-3-amino-4-(4-fluorophenyl)-1-furfurylthio-2-butanone hydrochloride (Compound No. 243 in Table 1)

IR(KBr, cm$^{-1}$): 2959, 1718, 1591 NMR(CD$_3$OD, δ): 3.0(dd, J=15 Hz, 8.5 Hz, 1H), 3.35(dd, J=15 Hz, 8.5 Hz, 1H), 3.36(d, J=15 Hz, 1H), 3.52(d, J=15 Hz, 1H), 3.77(s, 2H), 4.62(dd, J=8.3 Hz, 5.7 Hz, 1H), 6.26(d, J=3.2 Hz, 1H), 6.34(m, 1H), 7.12(dd, J=8.8 Hz, 7.5 Hz, 2H), 7.33(dd, 7.5 Hz, 5.3 Hz, 2H), 7.44(m, 1H)

EXAMPLE 65

Preparation of (S)-3-tert-butoxycarbonylamino-4-(2-chlorphenyl)-1-furfurylthio-2-butanone (Compound No. 247 in Table 1)

NMR(CDCl$_3$, δ): 1.39(s, 9H), 2.98(dd, J=15 Hz, 8.5 Hz, 1H), 3.30(dd, J=15 Hz, 8.5 Hz, 1H), 3.31(s, 2H), 3.69(s, 2H), 4.82(m, 1H), 5.08(d, J=5.8 Hz, 1H), 6.21(d, J=3.1 Hz, 1H), 6.29(m, 1H), 7.17–7.23(m, 3H), 7.32–7.42(m, 2H)

EXAMPLE 66

Preparation of (S)-3-amino-4-(2-chlorphenyl)-1-furfurylthio-2-butanone hydrochloride (Compound No. 249 in Table 1)

IR(KBr, cm$^{-1}$): 2835, 1724, 1587 NMR(CD$_3$OD, δ): 3.12(dd, J=15 Hz, 8.9 Hz, 1H), 3.33(d, J=15 Hz, 1H), 3.42(d, J=15 Hz, 1H), 3.52(dd, J=15 Hz, 8.9 Hz, 1H), 3.71(d, J=7.5 Hz, 1H), 3.76(d, J=7.5 Hz, 1H), 4.73(dd, J=8.9 Hz, 6.0 Hz, 1H), 6.25(d, J=2.8 Hz, 1H), 6.37(m, 1H), 7.30–7.41(m, 3H), 7.43(m, 1H), 7.51(m, 1H)

EXAMPLE 67

Preparation of (S)-3-tert-butoxycarbonylamino-4-(4-chlorphenyl)-1-furfurylthio-2-butanone (Compound No. 253 in Table 1)

NMR(CDCl$_3$, δ): 1.41(s, 9H), 2.92(dd, J=14 Hz, 7.2 Hz, 1H), 3.09(dd, J=14 Hz, 7.2 Hz, 1H), 3.23(s, 2H), 3.65(s, 2H), 4.71(q, J=7.1 Hz, 1H), 5.02(d, J=7.1 Hz, 1H), 6.19(m, 1H), 6.29(m, 1H), 7.07–7.11(m, 2H), 7.23–7.29(m, 2H), 7.39(m, 1H)

EXAMPLE 68

Preparation of (S)-4-(4-chlorphenyl)-1-furfurylthio-3-phenoxyacetylamino-2-butanone (Compound No. 256 in Table 1)

NMR(CDCl$_3$, δ): 3.0(dd, J=14 Hz, 6.5 Hz, 1H), 3.12(dd, J=14 Hz, 6.5 Hz, 1H), 3.19(s, 2H), 3.63(s, 2H), 4.48(s, 2H), 5.12(q, J=7.9 Hz, 1H), 6.19(m, 1H), 6.29(m, 1H), 6.84–6.89(m, 2H), 7.02–7.10(m, 4H), 7.18–7.35(m, 5H)

EXAMPLE 69

Preparation of (S)-3-tert-butoxycarbonylamino-1-furfurylthio-5-phenyl-2-pentanone (Compound No. 273 in Table 1)

NMR(CDCl$_3$, δ): 1.46(s, 9H), 1.86(m, 1H), 2.19(m, 1H), 2.86(t, J=7.7 Hz, 2H), 3.25(d, J=15 Hz, 1H), 3.33(d, J=15 Hz, 1H), 3.73(s, 2H), 4.52(m, 1H), 5.14(d, J=7.8 Hz, 1H), 6.20(d, J=2.6 Hz, 1H), 6.28(m, 1H), 7.13–7.38(m, 6H)

EXAMPLE 70

Preparation of (S)-1-furfurylthio-3-phenoxyacetylamino-5-phenyl-2-pentanone (Compound No. 277 in Table 1)

IR(neat, cm$^{-1}$): 3420, 3320, 1710, 1670 NMR(CDCl$_3$, δ): 1.94(m, 1H), 2.29(m, 1H), 2.60(m, 2H), 3.27(s, 2H), 3.71(s, 2H), 4.52(s, 2H), 4.96(m, 1H), 6.19(m, 1H), 1H), 6.28(m, 1H), 6.93–7.38(m, 12H)

EXAMPLE 71

Preparation of (S)-3-tert-butoxycarbonylamino-1-furfurylthio-4-(1-naphthyl)-2-butanone (Compound No. 282 in Table 1)

NMR(CDCl$_3$, δ): 1.40(s, 9H), 2.99(s, 2H), 3.49(d, J=7.5 Hz, 2H), 3.59(s, 2H), 4.87(q, J=7.5 Hz, 1H), 5.11(d, J=7.5 Hz, 1H), 6.13(m, 1H), 6.26(m, 1H), 7.26–7.42(m, 4H), 7.49–7.62(m, 2H), 7.77(d, J=7.9 Hz, 1H), 7.87(d, J=7.5 Hz, 1H), 8.15(d, J=7.2 Hz, 1H)

EXAMPLE 72

Preparation of (S)-1-furfurylthio-4-(1-naphthyl)-3-phenoxyacetylamino-2-butanone (Compound No. 286 in Table 1)

NMR(CDCl$_3$, δ): 2.89(d, J=15 Hz, 1H), 3.01(d, J=15 Hz, 1H), 3.54(m, 2H), 3.57(s, 2H), 4.39(d, J=15 Hz, 1H), 4.47(d, J=15 Hz, 1H), 5.25(q, J=7.4 Hz, 1H), 6.11(m, 1H), 6.24(m, 1H), 6.83(d, J=7.5 Hz, 2H), 7.02(t, J=7.5 Hz, 2H), 7.18–7.39(m, 6H), 7.50–7.62(m, 2H), 7.77(d, J=8.2 Hz, 1H), 7.87(d, J=7.5 Hz, 1H), 8.23(d, J=8.2 Hz, 1H)

EXAMPLE 73

Preparation of (S)-3-tert-butoxycarbonylamino-1-furfurylthio-4-(2-naphthyl)-2-butanone (Compound No. 290 in Table 1)

NMR(CDCl$_3$, δ): 1.39(s, 9H), 3.05–3.35(m, 4H), 3.63(s, 2H), 4.82(m, 1H), 5.09(d, J=6.8 Hz, 1H), 6.13(d, J=2.9 Hz, 1H), 6.26(m, 1H), 7.28–7.35(m, 2H), 7.42–7.52(m, 2H), 7.61(s, 1H), 7.70–7.85(m, 3H) J=8.2 Hz, 1H)

EXAMPLE 74

Preparation of (S)-1-furfurylthio-3-isobutoxycarbonylamino-4-(2-naphthyl)-2-butanone (Compound No. 291 in Table 1)

Melting Point: 84°–87° C. IR(KBr, cm$^{-1}$): 3330 1735, 1685 NMR(CDCl$_3$, δ): 0.88(d, J=6.7 Hz, 6H), 1.86(m, 1H), 3.16–3.35(m, 2H), 3.19(s, 2H), 3.62(s, 2H), 3.82(d, J=6.7 Hz, 2H), 4.91(q, J=7.5 Hz, 1H), 5.25(d, J=7.5 Hz, 1H), 6.13(m, 1H), 6.25(m, 1H), 7.24–7.34(m, 2H), 7.42–7.50(m, 2H), 7.61(s, 1H), 7.75–7.85(m, 3H)

EXAMPLE 75

Preparation of (S)-3-tert-butoxycarbonylamino-1-furfuryloxy-2-heptanone (Compound No. 298 in Table 1)

IR(KBr, cm$^{-1}$): 3349, 1709 NMR(CDCl$_3$, δ): 0.87(t, J=6.8 Hz, 3H), 1.13–1.37(m, 4H), 1.43(s, 9H), 1.45(m, 1H), 1.79(m, 1H), 4.17(d, J=18 Hz, 1H), 4.25(d, J=18 Hz, 1H), 4.46(m, 1H), 4.52(d, J=13 Hz, 1H), 4.58(d, J=13 Hz, 1H), 5.10(d, J=7.9 Hz, 1H), 6.30–6.39(m, 2H), 7.42(m, 1H)

EXAMPLE 76

Preparation of (S)-3-tert-butoxycarbonylamino-1-(3-thienylmethoxy)-2-heptanone (Compound No. 304 in Table 1)

IR(KBr, cm$^{-1}$): 3349, 1709 NMR(CDCl$_3$, δ): 0.88(t, J=6.9 Hz, 3H), 1.12–1.39(m, 4H), 1.43(s, 9H), 1.47(m, 1H), 1.79(m, 1H), 4.15(d, J=15 Hz, 1H), 4.23(d, J=15 Hz, 1H), 4.49(m, 1H), 4.57(d, J=12 Hz, 1H), 4.64(d, J=12 Hz, 1H), 5.11(d, J=7.8 Hz, 1H), 7.09(m, 1H), 7.25(m, 1H), 7.31(m, 1H)

EXAMPLE 77

Preparation of (S)-3-amino1-(3-thienylmethoxy)-2-heptanone hydrochloride (Compound No. 306 in Table 1)

IR(KBr, cm$^{-1}$): 3441, 1732, 1587 NMR(CD3OD, δ): 0.93(t, J=6.9 Hz, 3H), 1.17–1.59(m, 4H), 1.77(m, 1H), 1.98(m, 1H), 4.27(d, J=15 Hz, 1H), 4.34(d, J=15 Hz, 1H), 4.35(m, 1H), 4.60(d, J=15 Hz, 1H), 4.66(d, J=15 Hz, 1H), 7.12(m, 1H), 7.37–7.51(m, 2H)

EXAMPLE 78

Preparation of (S)-3-tert-butoxycarbonylamino-1-furfuryloxy-4-phenyl-2-butanone (Compound No. 316 in Table 1)

NMR(CDCl$_3$, δ): 1.39(s, 9H), 2.83–3.14(m, 2H), 3.94(d, J=16 Hz, 1H), 4.18(d, J=16 Hz, 1H), 4.38–4.73(m, 3H), 5.11(m, 1H), 6.27(d, J=2.7 Hz, 1H), 6.32(m, 1H), 7.05–7.40(m, 6H)

EXAMPLE 79

Preparation of (S)-3-tert-butoxycarbonylamino-1-(N-furfuryl-N-methylamino)-4-phenyl-2-butanone (Compound No. 377 in Table 1)

NMR(CDCl$_3$, δ): 1.40(s, 9H), 2.27(s, 3H), 2.85–3.08(m, 2H), 3.07(d, J=18 Hz, 1H), 3.36(d, J=18 Hz, 1H), 3.55(d, J=14 Hz, 1H), 3.65(d, J=14 Hz, 1H), 4.67(q, J=7.2 Hz, 1H), 5.13(d, J=7.2 Hz, 1H), 6.17(d, J=3.0 Hz, 1H), 6.31(m, 1H), 7.07–7.40(m, 6H)

EXAMPLE 80

Preparation of (S)-3-tert-butoxycarbonylamino-1-furfurylthio-4-(2-thienyl)-2-butanone (Compound No. 436 in Table 1)

NMR(CDCl$_3$, δ): 1.44(s, 9H), 3.15–3.42(m, 4H), 3.68(s, 2H), 4.71(dt, J=7.1 Hz, 6.5 Hz, 1H), 5.11(d, J=7.1 Hz, 1H), 6.19(d, J=2.9 Hz, 1H), 6.29(m, 1H), 6.82(d, J=3.1 Hz, 1H), 6.93(m, 1H), 7.18(d, J=5.8 Hz, 1H), 7.36(m, 1H)

TEST EXAMPLE

Measurement of Inhibitory Activity against Thiol Protease

Through the known method disclosed in Journal of Biological Chemistry, vol. 259, page 3210, 1984, m-calpain was purified from a brain of rat. The inhibitory activity against it was measured and determined according to the method disclosed in Journal of Biological Chemistry, vol. 259, page 12489, 1984. The results are set forth in Table 2 below, indicating that the compounds according to the present invention exhibit strong inhibitory activity against thiol protease.

TABLE 2

| Example No. (Compound No. in Table 1) | IC$_{50}$ (μm) |
|---|---|
| 17 (No. 86) | 12.2 |
| 18 (No. 87) | 13.0 |
| 38 (No. 171) | 17.0 |
| 58 (No. 216) | 4.5 |
| 60 (No. 219) | 14.5 |

What we claim is:

1. An aminoketone derivative of the following formula or a pharmaceutically acceptable salt thereof:

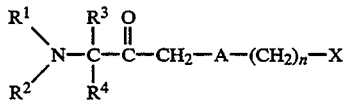

wherein,
R$^1$ is hydrogen

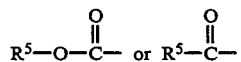

wherein R$^5$ is a member selected from the group consisting of
(a) C$_1$ to C$_{20}$ alkyl which is unsubstituted or is substituted by at least one substituent selected from the group consisting of (1) C$_6$ to C$_{14}$ aryl, (2) fluorenyl, (3) a C$_3$ to C$_9$ heterocyclic group containing a hetero atom selected from the group of nitrogen, sulfur and oxygen, which group may be substituted by C$_6$ to C$_{10}$ arylamino or oxo, (4) C$_3$ to C$_{15}$ cycloalkyl, (5) C$_3$ to C$_{15}$ cycloalkyloxy, (6) C$_6$ to C$_{14}$ aryloxy which may be substituted by C$_l$ to C$_3$ alkoxy, halogen, C$_1$ to C$_3$ alkyl or trifluoromethyl, (7) C$_7$ to C$_{20}$ aralkyloxy, (8) C$_6$ to C$_{14}$ arylthio, (9) hydroxyl and (10) C$_2$ to C$_{10}$ alkanoyloxy,
(b) C$_2$ to C$_{10}$ alkenyl which is unsubstituted or is substituted by (1) C$_6$ to C$_{10}$ aryl which may be substituted by C$_1$ to C$_3$ alkoxy, or (2) thiazolyl which may be substituted by C$_2$ to C$_5$ alkanoylamino,
(c) C$_6$ to C$_{14}$ aryl which is unsubstituted or is substituted by C$_6$ to C$_{10}$ aryloxy, and
(d) a 5 or 6 membered heterocyclic group containing at least one hetero atom selected from the group consisting of nitrogen, sulfur and oxygen, which heterocyclic group is unsubstituted or is substituted by oxo, R$^2$ and R$^4$ are independently hydrogen or C$_1$ to C$_5$ alkyl, R$^3$ is (a) hydrogen, or (b) C$_1$ to C$_{20}$ alkyl which is unsubstituted or is substituted by (1) C$_2$ to C$_4$ alkoxycarbonyl, (2) C$_3$ to C$_{10}$ cycloalkyl, (3) C$_6$ to C$_{14}$ aryl which may be substituted by halogen or thienyl, or R$^3$ when taken together with R$^4$, forms C$_1$ to C$_{10}$ alkylene, A is oxygen, sulfur or

wherein R$^6$ is hydrogen or C$_1$ to C$_5$ alkyl, n is an integer of 1 to 10, and X is a 5 to 6 membered heterocyclic group containing at least one hetero atom selected from the group consisting of nitrogen, sulfur and oxygen which heterocyclic group is unsubstituted or is substituted by oxo.

2. A compound according to claim 1 wherein R$^1$ is hydrogen,

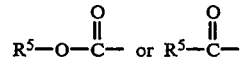

wherein R$^5$ is a member selected from the group consisting of
(a) C$_1$ to C$_{10}$ alkyl which is unsubstituted or is substituted by at least one substituent selected from the group consisting of (1)C$_6$ to C$_{14}$ aryl, (2) fluorenyl, (3) thiazolyl which may be substituted by phenylamino, (4) benzofuranyl, (5) chromanyl, (6) 4-oxochromenyl, (7) C$_3$ to C$_{10}$ cycloalkyloxy, (8) C$_6$ to C$_{14}$ aryloxy which may be substituted by C$_1$ to C$_3$ alkoxy, halogen, C$_1$ to C$_3$ alkyl or trifluoromethyl, (9) C$_7$ to C$_{15}$ aralkyloxy, (10) C$_6$ to C$_{10}$ arylthio and (11) C$_2$ to C$_6$ alkanoyloxy,
(b) C$_2$ to C$_6$ alkenyl which is unsubstituted or is substituted by (1) C$_6$ to C$_{10}$ aryl which may be substituted by C$_1$ to C$_3$ alkoxy or (2) thiazolyl which may be substituted by C$_2$ to C$_5$ alkanoylamino,
(c) C$_6$ to C$_{10}$ aryl which is unsubstituted or is substituted by C$_6$ to C$_{10}$ aryloxy, and
(d) pyrrolidinyl which may be substituted by oxo, and X is (1) furyl, (2) thienyl, (3) oxazolidinyl which may be substituted by oxo or (4) pyridinyl.

3. A compound according to claim 1 wherein R$^1$ is

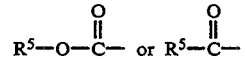

wherein R$^5$ is a member selected from the group consisting of
(a) C$_1$ to C$_5$ alkyl which is unsubstituted or is substituted by C$_6$ to C$_{10}$ aryloxy which may be substituted by C$_1$ to C$_3$ alkoxy, and (b) $C_2$ to $C_5$ alkenyl which is unsubstituted or is substituted by $C_6$ to $C_{10}$ aryl which may be substituted by $C_1$ to $C_3$ alkoxyl, $R^2$ and $R^4$ are hydrogen, $R^3$ is $C_1$ to $C_{10}$ alkyl which is unsubstituted or is substituted by $C_6$ to $C_{10}$ aryl, A is sulfur, n is an inter of 1 to 3, and X is furyl or thienyl.

4. A pharmaceutical composition for treating diseases resulting from abnormal sthenia of thiol protease which comprises an effective amount of a compound or salt thereof as defined in claim 1 and a pharmaceutically acceptable carrier therefor.

5. A method for the treatment of a disease resulting from abnormal sthenia of thiol protease which comprises administering to a patient in need of such treatment an effective amount of a compound or a salt thereof as defined in claim 1.

* * * * *